(12) United States Patent
Davis et al.

(10) Patent No.: US 6,261,787 B1
(45) Date of Patent: *Jul. 17, 2001

(54) BIFUNCTIONAL MOLECULES FOR DELIVERY OF THERAPEUTICS

(75) Inventors: Pamela B. Davis, Cleveland heights; Thomas W. Ferkol, Jr., Concord, both of OH (US); Elizabeth Eckman, Ponte Vedra Beach, FL (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/264,032

(22) Filed: Mar. 8, 1999

Related U.S. Application Data

(63) Continuation-in-part of application No. 08/957,333, filed on Oct. 24, 1997, now Pat. No. 6,072,041, which is a continuation-in-part of application No. 08/655,705, filed on Jun. 3, 1996, now Pat. No. 5,972,900, and a continuation-in-part of application No. 08/656,906, filed on Jun. 3, 1996, now Pat. No. 5,972,901.

(51) Int. Cl.[7] ........................ G01N 33/53; G01N 33/567; C07K 16/00; A61K 38/00; C07H 21/02
(52) U.S. Cl. ........................ 435/7.1; 435/7.21; 435/69.7; 530/391.1; 530/391.7; 530/402; 530/807; 530/866; 514/12; 536/23.1
(58) Field of Search ........................ 530/866, 867, 530/402, 391.1, 391.7; 514/12; 536/23.1; 435/7.1, 7.21, 69.7

(56) References Cited

U.S. PATENT DOCUMENTS

| | | | |
|---|---|---|---|
| 5,100,788 | 3/1992 | Lofdahl et al. | 435/69.7 |
| 5,108,921 | 4/1992 | Low et al. | 435/260.1 |
| 5,521,291 | 5/1996 | Curiel et al. | 530/391.7 |
| 5,763,192 | 6/1998 | Kauffman et al. | 435/7.1 |
| 5,871,974 | 2/1999 | Huse | 435/69.7 |

OTHER PUBLICATIONS

Ernst Wagner et al. "Transferrin–polycation–DNA complexes: The effect of polycations on the structure of the complex and DNA delivery to cells" Proc. Natl. Acad. Sci. USA vol. 88, pp. 4255–4259, May 1991.

Elizabeth Eckman et al., Pediatric Pulmonology 14 (Suppl.): A229 "Targeting the Polymeric Immunoglobulin Receptor as a Means of Directing Therapeutic Proteins to the Airway" 1997.

Elizabeth Eckman et al., Pediatric Pulmonology 13 (Suppl.) A242 "Structure and Function of Anti–Human Secretory Component FV/Human Alpha1–Antitrypsin Fusion Proteins" 1996.

Amedeo Caflisch "Computational combinatorial ligand design: Application to human a–thrombin" Journal of Computer–Aided Molecular Design 10 (1996) 372–396.

(List continued on next page.)

Primary Examiner—Hankyel T. Park
(74) Attorney, Agent, or Firm—Banner & Witcoff LTD

(57) ABSTRACT

A bifunctional molecule consisting of a therapeutic molecule and a ligand which specifically binds a transcytotic receptor can be transported specifically from the basolateral surface of epithelial cells to the apical surface. This approach provides the ability to deliver a therapeutic molecule directly to the apical surface of the epithelium, by targeting the transcytotic receptor with an appropriate ligand. Thus, the highest concentration of the therapeutic molecule will be at the apical surface, where it can have the greatest therapeutic effect.

16 Claims, 18 Drawing Sheets

OTHER PUBLICATIONS

Moon and Howe "Computer Design of Bioactive Molecules: A Method for Receptor–Based de Novo Ligand Design" Proteins: Structure, Function and Genetics 11:314–328 (1991).

Aya Jakobovits "Production of fully human antibodies by transgenic mice" Current Opinion in Biotechnology 1995 6:561–566.

Wagner et al. "The diversity of antigen–specific monoclonal antibodies from transgenic mice bearing human immunoglobulin gene miniloci" Eur. J. Immunol. 1994, 24:2672–2681.

Lonberg et al. "Antigen–specific human antibodies from mice comprising four distinct genetic modifications" Nature vol. 368 Apr. 28, 1994 pp. 856–859.

Neuberger & Bruggemann "Mice perform a human repertoire" Nature, vol. 386, Mar. 1997 pp. 25–26.

Mendez et al. "Functional transplant of megabase human immunoglobulin loci recapitulates human antibody response in mice" Nature Genetics vol. 15, Feb. 1997 pp. 146–156.

Aya Jakobovits Production of Antigen–Specific Human Antibodies from Mice Engineered with Human Heavy and Light Chain YACs, Annals of the New York Academy of Sciences, 1995 vol. 764 pp. 525–535.

L.L. Green "Antigen–specific human monoclonal antibodies from mice engineered with human Ig heavy and light chain YACs" Nature Genetics 1994 vol. 7 (1) pp. 13–21.

Powers et al. "Specificity of Porcine Pancreatic Elastase, Human Leukocyte Elastase and Cathepsin G" Biochimica et Biophysica Acta, 485 (1977) pp. 156–166.

Bode et al. "Human Leukocyte and Porcine Pancreatic Elastase: X–ray Crystal Structures, Mechanism, Substrate Specifcity, and Mechanism–Based Inhibitors" Biochemistry, vol. 28, No. 5 Mar. 7, 1989 pp. 1951–1963.

Nakajima et al. "Mapping the Extended Substrate Binding Site of Cathepsin G and Human Leukocyte Elastase" The Journal of Biological Chemistry, vol. 254, No. 10, May 25, 1979 pp 4027–4032.

Zimmerman and Ashe "Substrate Specificity of the Elastase and the Chymotrypsin–Like Enzyme of the Human Granulocyte" Biochmicia et Biophysica Acta, 480 (1977) pp. 241–245.

Ferkol et al. Receptor–mediated gene transfer into macrophages, Proc. Natl. Acad. Sci. USA. Jan. 1996, vol. 93, No. 1, pp. 101–105.

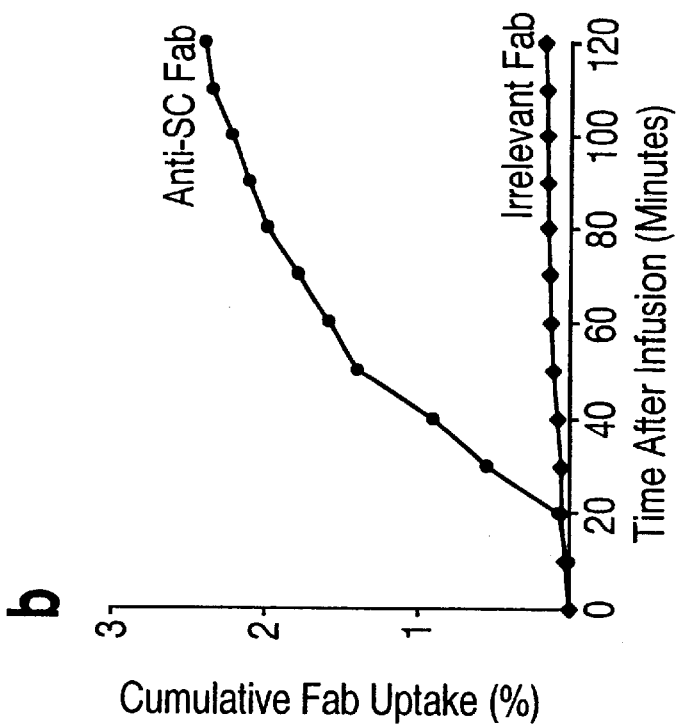
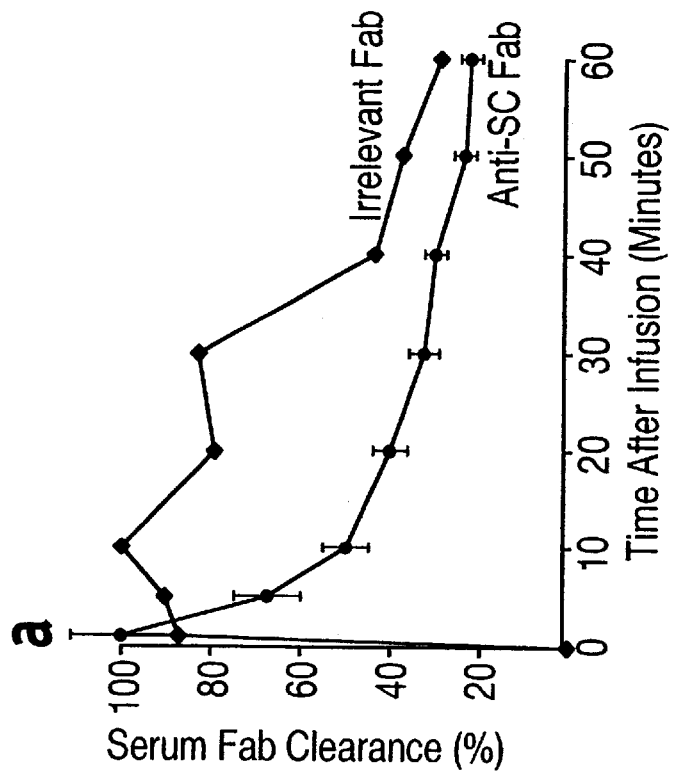
FIG. 2

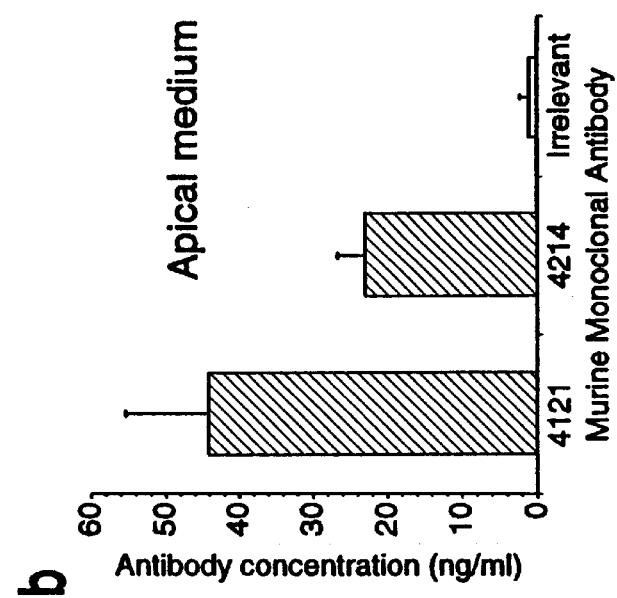
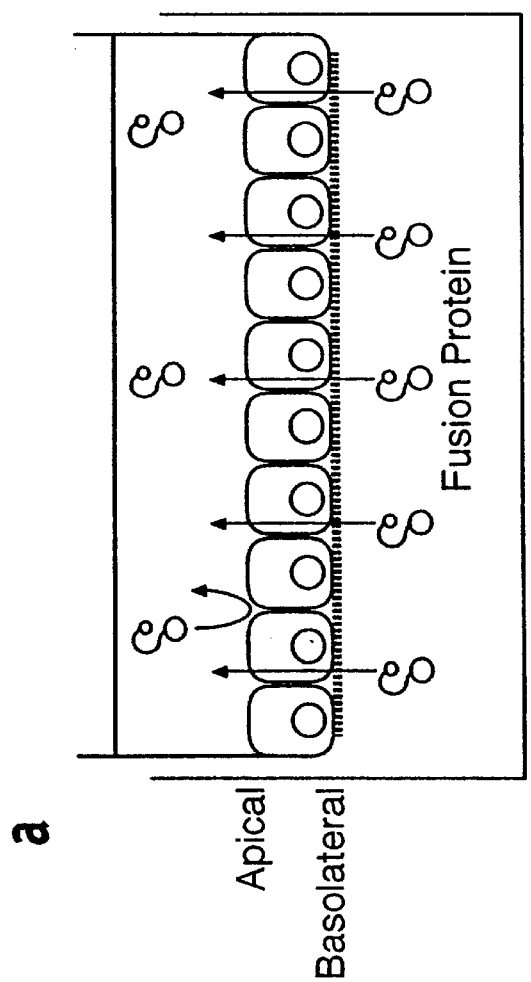
FIG. 10

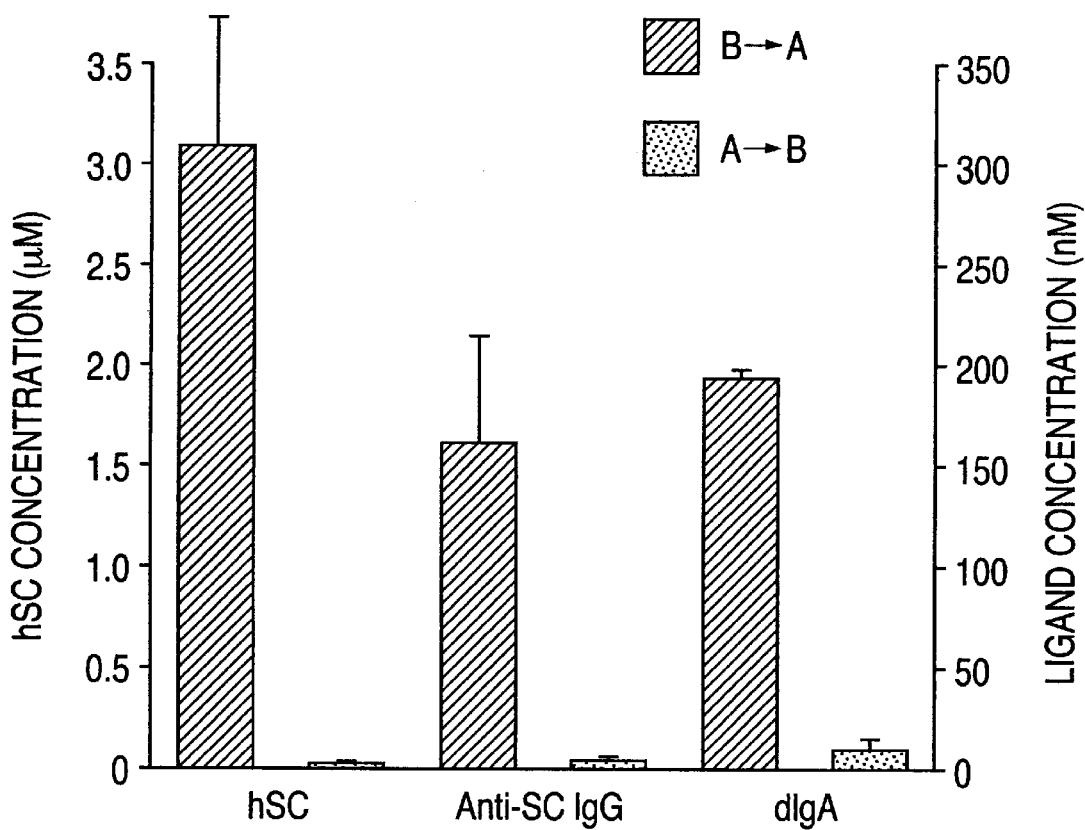

BIFUNCTIONAL MOLECULES FOR DELIVERY OF THERAPEUTICS

This application is a continuation-in-part of U.S. Ser. No. 08/957,333 filed Oct. 24, 1997, the disclosure of which is expressly incorporated herein by reference, now U.S. Pat. No. 6,072,041 which is a continuation-in-part of U.S. Ser. No. 08/655,705, filed Jun. 3, 1996, now U.S. Pat. No. 5,972,900, and U.S. Ser. No. 08/656,906, filed Jun.3, 1996, now U.S. Pat. No. 5,972,901.

BACKGROUND OF THE INVENTION

The epithelium is the first line of defense against a variety of pathogens. Epithelial cells produce low molecular weight antimicrobial peptides, antibacterial enzymes, and antiproteases. However, optimal methods of specifically targeting therapeutic molecules to epithelial cells have been lacking in the art. There is a continuing need in the art for methods of providing therapeutic agents to respiratory epithelia cells in diseases such as cyptic fibrosis, asthma, and emphysema, and to intestinal epithelial cells, for example, in inflammatory bowel diseases.

SUMMARY OF THE INVENTION

It is an object of the invention to provide bifunctional molecules useful for delivery of therapeutic molecules and methods for delivering therapeutic molecules to cells. These and other objects of the invention are provided by one or more embodiments as described below.

In one embodiment the invention provides a fusion protein. The fusion protein comprises a single chain Fv molecule directed against a human transcytotic receptor covalently linked to a therapeutic protein. The therapeutic protein may be, for example, $\alpha_1$-antitrypsin, a cytokine, such as interleukin-2 or interleukin-10, or a peptide antibiotic. Suitable peptide antibiotics include aerosporin, amphomycin, aspartocin, bacitracins, caperomycins, colistins, dactinomycins, glumamycins, gramicidin D, gramicidin S, mikamycin B, polymixins, pristinamycin, siomycin, staphylomycin S, thiostrepton, tyrocidines, tyrothricin, valinomycin, vancomycin, veramycin B. Any therapeutic protein which one wants delivered to epithelial cells may be used. The fusion protein may further comprise a linker region of less than 50, 40, 30, 20, or 10 amino acid residues. The linker can be covalently linked to and between the single chain Fv molecule and the therapeutic protein.

Also provided according to another aspect of the invention is a method of delivering a therapeutic protein to an epithelial cell. The method comprises: administering a fusion protein as described above to a patient, whereby the therapeutic protein is delivered to an epithelial cell. The epithelial cell may be an airway epithelial cell or an intestinal lumen cell, for example. The liver may also be targeted. The administration mode may be any known in the art. However, inhalation and intravenous administration have been found to be both convenient and efficient.

Nucleic acid molecules are also provided by the present invention. These encode a fusion protein comprising a single chain Fv molecule directed against a transcytotic receptor covalently linked to a therapeutic protein. The therapeutic protein may be, for example, $\alpha_1$-antitrypsin, a cytokine, such as interleukin-2 or interleukin-10, or a peptide antibiotic. Any therapeutic protein which one wants delivered to epithelial cells may be used. The fusion protein may further comprise a linker region of less than 50, 40, 30, 20, or 10 amino acid residues. The linker can be covalently linked to and between the single chain Fv molecule and the therapeutic protein. Host cells and vectors for replicating the nucleic acid molecules and for expressing the encoded fusion proteins are also provided. Any vectors or host cells may be used, whether prokaryotic or eukaryotic. Many vectors and host cells are known in the art for such purposes. It is well within the skill of the art to select an appropriate set for the desired application.

The invention also provides a bifunctional molecule comprising a ligand coupled to a non-protein therapeutic molecule. The ligand specifically binds to a transcytotic receptor, such as the human secretory component of polymeric immunoglobulin receptor. The coupling is carried out such that the ligand can bind to the transcytotic receptor.

Another embodiment of the invention provides a method of delivering a therapeutic molecule to an epithelial cell. A bifunctional molecule is administered to a patient. The bifunctional molecule comprises a ligand coupled to a non-protein therapeutic molecule. The ligand specifically binds to a transcytotic receptor, such as the human secretory component of polymeric immunoglobulin receptor. The therapeutic molecule is thereby delivered to an epithelial cell. The epithelial cell may be an airway epithelial cell or an intestinal lumen cell, for example. The liver may also be targeted. The administration mode may be any known in the art. However, inhalation and intravenous administration have been found to be both convenient and efficient.

The present invention thus provides an efficient means of delivering therapeutic molecules to body parts which are often inaccessible or difficult to access reliably.

BRIEF DESCRIPTION OF THE DRAWINGS

FIG. 2. Clearance and hepatic uptake of the anti-rat SC Fab. Blood (FIG. 2A) and bile (FIG. 2B) were collected every 10 minutes after injection with 50 µg of irrelevant (n=5) or anti-rat SC Fab (n=5), and analyzed for rabbit-derived antibodies using an ELISA. The Fab levels are represented as the percentage of peak serum concentrations.

(FIG. 5A) Construction of the anti-hSC Fv protein by PCR. Total cellular RNA was extracted from the antibody-producing cells and treated with Moloney Murine Leukemia Virus reverse transcriptase using random hexamers as primers. The resultant cDNA were screened for the $V_L$ and $V_H$ domains using different oligonucleotide primers, and these sequences were amplified by the PCR. The $V_L$ and $V_H$ domains were then amplified to include linker sequences that permitted splicing using a PCR technique called overlap extension to produce the full-length gene encoding the single chain Fv. (FIG. 5B) Schematic diagram of the structure of the anti-human SC Fv/human $A_1AT$ chimeric genes. (FIG. 5C) Restriction endonuclease digestion of plasmids containing the anti-human SC Fv/human $A_1AT$ chimeric gene. One microgram of plasmid DNA was digested with ClaI/HindIII (lane 1), ClaI/XbaI (lane 2), and HindIII (lane 3). Molecular weight markers are indicated in the right lane.

FIG. 10. (FIG. 10A) Schematic diagram of the cell model system, showing the transport of fusion proteins or antibodies across polarized MDCK cells expressing the pIgR in the basolateral-to-apical direction. (FIG. 10B) Transport of the anti-human SC antibodies across the MDCK cell monolayer that express the pIgR. Apical media was collected over six hours after addition of the antibodies to the basolateral media, and the concentration (ng/ml) of the mouse-derived antibody was determined by ELISA. The anti-human SC antibodies (4121 and 4214) were effectively transported from the basolateral surface to the apical media, whereas an irrelevant antibody (D8) did not. None of the antibodies were transported in the apical-to-basolateral direction.

FIG. 19. Transport of ligands across primary airway epithelial cells in vitro.

DETAILED DESCRIPTION OF THE INVENTION

Figure 1:
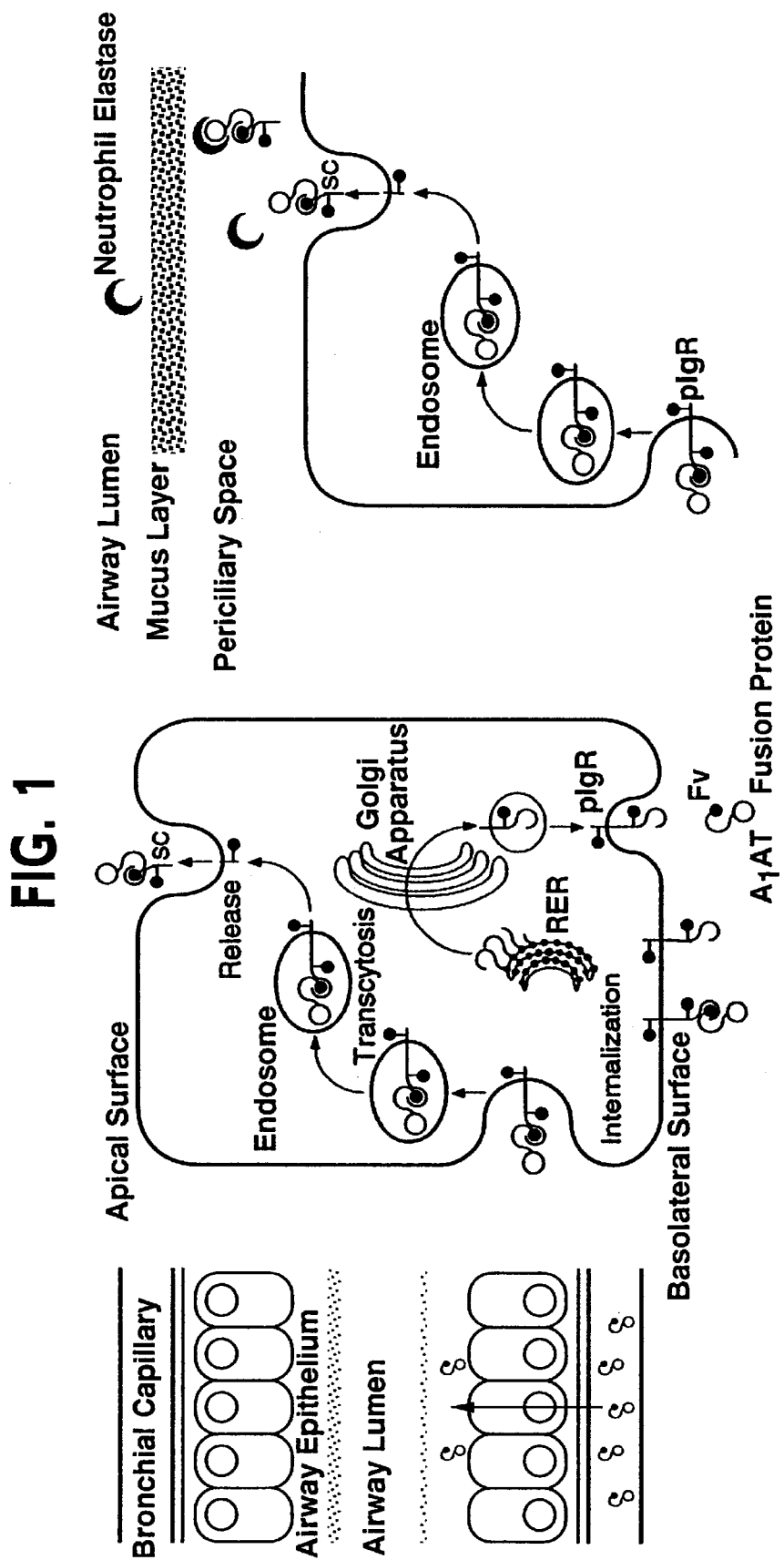
FIG. 1. Schematic diagrams showing the transport of fusion proteins from the systemic circulation to the epithelial surface (left). The fusion protein is bound to pIgR at the basolateral surface and is trafficked to the apical membrane (center). Once it reaches the this surface, the fusion is released into the airway lumen, attached to secretory component of the polymeric immunoglobin receptor (SC), where the antiprotease component binds and neutralizes elastase (right).
Figure 3:
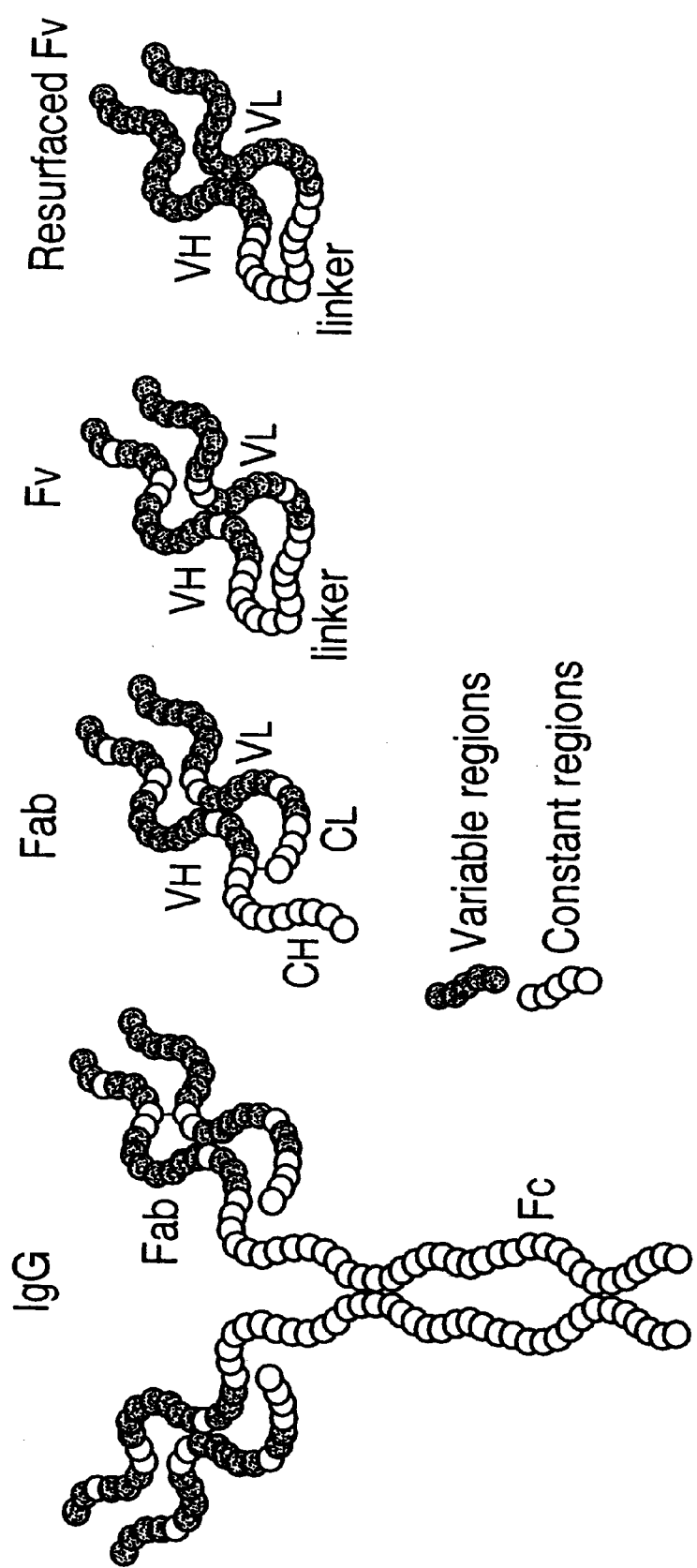
FIG. 3. Schematic diagram of antibodies, Fab fragments, and single chain Fv fragments, showing the variable ($V_L$ and $V_H$) and constant ($C_L$ and $C_H$) regions.
Figure 4:
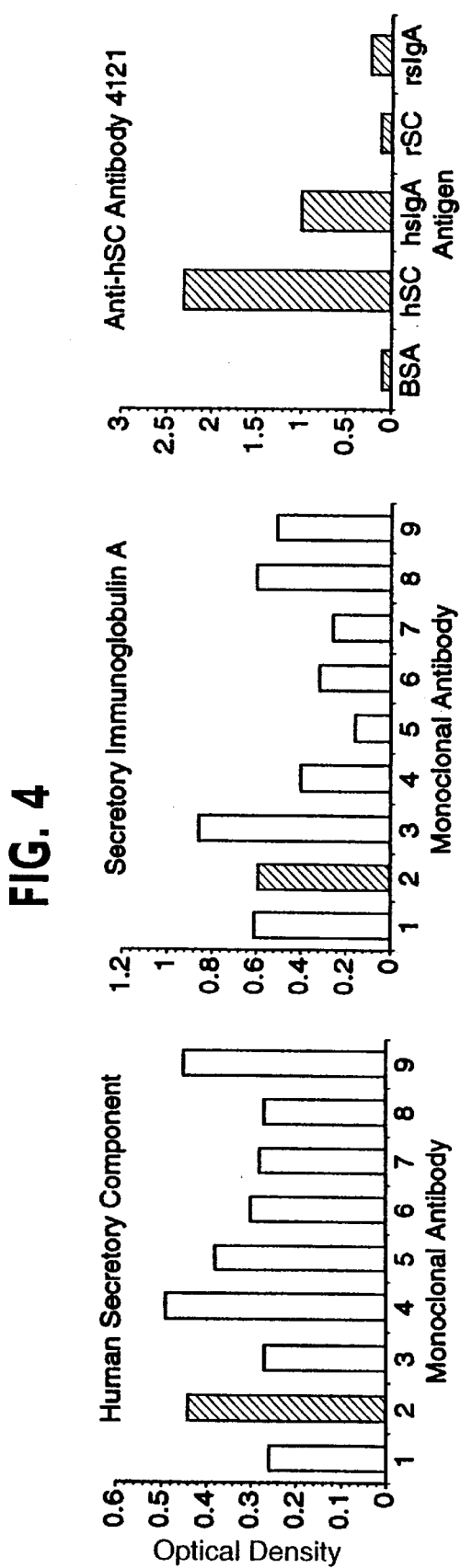
FIG. 4. Binding of anti-human SC monoclonal antibodies. (left) Relative binding of antibodies to purified human SC, as measured by ELISA. Monoclonal antibody 4121 is indicated by solid column. (center) Relative binding of antibodies to sIgA. (right) Additional characterization of anti-human SC antibody 4121. Note the difference in affinity of the antibody to human and rat SC.

We have discovered that one can efficiently deliver functional therapeutic molecules to cells which bear transcytotic receptors, which can deliver the therapeutic molecule to the other side of a cell. Such receptors include the immunoglobulin transporting receptors in the gut of infants, immunoglobulin transporting receptors in the placenta, and the polymeric immunoglobulin receptor (pIgR). For example, the pIgR is trafficked to the basolateral surface of epithelial cells where it is specifically adapted for the internalization and nondegradative transfer of polymeric antibodies (21), i.e., dimeric immunoglobulin A (dIgA) and pentameric immunoglobulin M (pIgM). The receptor-ligand complex is transported across the cell to the apical surface, where the receptor is cleaved, releasing dIgA bound to the ectoplasmic domain of the receptor, or secretory component (SC), into the lumen (FIG. 1). The receptor does not require the natural ligand for endocytosis, and antibodies (or Fab fragments) directed against human SC also undergo efficient transcytosis (22). In humans, the receptor is expressed, for example, in airway epithelial cells which reach the luminal surface and in cells of the submucosal glands, especially serous cells (23). Thus, the pIgR in humans is well-suited for the delivery of therapeutic molecules to bronchi and bronchioles.

For example, this receptor permits the delivery of the therapeutic molecules, such as antiprotease, to the apical surface of the respiratory epithelium. The trafficking pattern of the antibody-based therapeutic molecule can also be used to deliver relevant therapeutic molecules to other tissues. For example, the bile ducts and intestine are relatively inaccessible from the luminal surface and can be targeted in this manner. The targeting of therapeutic molecules by the pIgR in humans provides an additional level of safety in vivo, since a therapeutic molecule not delivered to the lung, for example, will be transported to the intestinal lumen, through either the enterocyte or in bile, where it will be excreted.

The expression and tissue distribution of the pIgR in rodents is different from that observed in humans (35, 36). In rodents, the expression of the receptor is significantly greater in the liver than lung, based on the production of SC. Moreover, fifty per cent of the radiolabeled dIgA injected into the systemic circulation is rapidly transported from blood to bile by rat hepatocytes, while less than two per cent was detected in the lung after two hours (37). The clearance and tissue distribution of rabbit-derived, anti-SC Fab antibodies in rats are similar to the natural ligand. Yet, rodents can still serve as a model for the delivery of therapeutic molecules to epithelia.

Another useful receptor which can be targeted is the serpin-enzyme complex (sec) receptor. This receptor is found on macrophages. Targeting the sec receptor would allow the delivery, e.g., of anti-tuberculous antibiotics into macrophages, where tubercle bacilli reside.

In one embodiment of the invention, a bifunctional molecule which comprises a ligand specific for a transcytotic receptor is used to deliver the therapeutic molecule to its target. Any ligand comprising a binding site for a transcytotic receptor can be used to construct the bifunctional molecule. A convenient transcytotic receptor ligand is an antigen binding site of an antibody or antibody-derived molecule. The smallest fragment to bear the antigen binding site is the Fv portion of an antibody, a 26 kDa heterodimer consisting of the amino-terminal variable domains of the heavy and light chains (26). The antigen binding moiety can be located in a whole antibody, antibody fragment, or subfragment. Antibodies can be whole immunoglobulin (IgG) of any class, e.g., IgG, IgM, IgA, IgD, IgE, chimeric antibodies or hybrid antibodies with dual or multiple antigen or epitope specificities, or fragments, such as F(ab')$_2$, Fab', Fab and the like, including hybrid fragments. Any immunoglobulin or any natural, synthetic, or genetically engineered protein that acts like an antibody by binding to the transcytotic receptor can be used to target the therapeutic molecule.

Preparations of polyclonal antibodies can be made using standard methods which are well known in the art. Antibodies can include antiserum preparations from a variety of commonly used animals, e.g., goats, primates, donkeys, swine, rabbits, horses, hens, guinea pigs, rats, or mice, and even human antisera after appropriate selection and purification. Animal antisera are raised by inoculating the animals with immunogenic epitopes of the transcytotic receptor by conventional methods, bleeding the animals, and recovering serum or an immunoglobulin-containing serum fraction.

Hybridoma-derived monoclonal antibodies (human, monkey, rat, mouse, or the like) are also suitable for use in the present invention and have the advantage of high specificity. They are readily prepared by what are now generally considered conventional procedures for immunization of mammals with an immunogenic transcytotic receptor preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, as it is primarily the specificity of the antibodies for the transcytotic receptor that affects their utility in the present invention.

Single-chain antibodies can also be prepared. Single-chain antibodies which specifically bind to transcytotic receptors can be isolated, for example, from single-chain immunoglobulin display libraries, as is known in the art. The library is "panned" against amino acid sequences of the receptor, and a number of single chain antibodies which bind with high-affinity to different epitopes of the receptor can be isolated. Hayashi et al., 1995, Gene 160:129–30. Single-chain antibodies can also be constructed using a DNA amplification method, such as the polymerase chain reaction (PCR), using hybridoma cDNA as a template. Thirion et al., 1996, Eur. J. Cancer Prev. 5:507–11.

Single-chain antibodies can be mono- or bispecific, and can be bivalent or tetravalent. Construction of tetravalent, bispecific single-chain antibodies is taught, for example, in Coloma and Morrison, 1997, Nat. Biotechnol. 15:159–63. Construction of bivalent, bispecific single-chain antibodies is taught inter alia in Mallender and Voss, 1994, J. Biol. Chem. 269:199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, Int. J. Cancer 61:497–501; Nicholls et al., 1993, J. Immunol. Meth. 165:81–91.

Monoclonal and other antibodies can also be "humanized" in order to prevent a patient from mounting an immune response against the antibody when it is used therapeutically in the bifunctional molecule. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafting of entire complementarity determining regions. Alternatively, one can produce humanized antibodies using recombinant methods, as described in GB2188638B. Antibodies which specifically bind to transcytotic receptors such as pIgR can contain antigen binding sites which are either partially or fully humanized, as disclosed in U.S. Pat. No. 5,565,332.

Rodents, such as mice and rats, can be genetically engineered to produce a large repertoire of human antibodies, to provide transcytotic receptor ligands. Segments of human immunoglobulin loci can be introduced into the germlines of these rodents. Either miniloci, containing 1–2 VH segments, or large continuous fragments of human heavy and light immunoglobulin loci can be used. If desired, gene targeting can be used to create rodents which do not make rodent antibodies. The engineered rodents produce fully human antibodies. In particular, human monoclonal antibodies with high affinity and specificity against a wide variety of antigens, including human antigens, can be produced. The human antibodies can then be used to provide transcytotic receptor ligands for use in bifunctional molecules of the invention. Methods of producing fully human antibodies from transgenic rodents are well known in the art (86–92).

Other types of antibodies can be constructed and used to construct the bifunctional molecules of the invention. For example, chimeric antibodies which comprise portions derived from two different species, such as a human constant region and a murine variable or binding region, can be constructed. The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins. Chimeric antibodies can be constructed as disclosed in WO 93/03151. Binding proteins which are derived from immunoglobulins and which are multivalent and multispecific, such as the "diabodies" described in WO 94/13804, can also be prepared.

Antibodies can be purified by methods well known in the art. For example, antibodies can be affinity purified by passing the antibodies over a column to which a transcytotic receptor is bound. The bound antibodies can then be eluted from the column, using a buffer with a high salt concentration.

Transcytotic receptor ligands can also be produced, for example, using a library of expression vectors which contain stochastically generated polynucleotide sequences. Host cells containing the expression vectors are cultured so as to produce polypeptides encoded by the polynucleotide sequences. The polypeptides can then be screened for the ability to bind to a transcytotic receptor using protein binding assays known in the art, such as electrophoresis through a non-denaturing gel, column chromatography, the yeast two-hybrid assay, and the like. This method of generating ligands is taught in U.S. Pat. No. 5,763,192, which is incorporated herein by reference. Computer-aided molecular design can also be used to generate ligands for transcytotic receptors (93, 94).

Ligands for a transcytotic receptor can be coupled to a variety of therapeutic molecules for targeted delivery to a cell. Classes of therapeutic molecules which can be coupled include steroids, proteins, carbohydrates, essential amino acids, vitamins, alkaloids, glycosides, lipids, radioisotopes, detectable labels, chelators, boron compounds, toxins, and the like. Therapeutic molecules with effects which include, but are not limited to, fungistatic, mycobacteriostatic, bacteriostatic, chemotherapeutic, antiviral, schistosomicidal, trypanocidal, leprostatic, pesticidic, parasiticide, nutritional, hormonal, anesthetic, bronchodilator, vasoconstrictor, vasodilator, antacid, laxative, emetic, antiemetic, adsorbent, digestant, antihistamine, antispasmodic, antineoplastic, antiseptic, antinauseant, antibiotic, diagnostic, cathartic, antitussive, muscle relaxant, sedative, anti-inflammatory, adrenergic antagonist or agonist, muscarinic antagonist or agonist, immunosuppressive, diuretic, antiflatulent, weight reducing, or expectorant effects can be effectively targeted by coupling such molecules to a transcytotic receptor ligand.

The therapeutic molecule to be targeted can be coupled to the transcytotic ligand using standard chemical conjugation techniques as is appropriate for the particular therapeutic molecule being coupled. Methods of coupling a protein, such as an antibody or other protein ligand, to a second molecule are well known in the art and are described, for example, in U.S. Pat. Nos. 5,082,928, 5,057,313, 4,671,958, 5,663,306, and 5,106,951, which are incorporated herein by reference. Reactions which can be used include esterification, amidation, mixed anhydride formation, hemiacetal formation, periodate coupling, and etherization.

The ligand and the therapeutic molecule should be coupled in such a way that the binding of the ligand to the transcytotic receptor is not impaired. The coupling can be by means of a cleavable link or a non-cleavable link, depending upon whether the therapeutic molecule is more effective when released in its native form or whether the pharmaceutical activity of the therapeutic molecule can be maintained while linked to the ligand. The therapeutic molecule can be directly linked to a transcytotic receptor ligand through nucleophilic substitution of certain groups on the ligand, such as carboxyl or sulfhydryl groups or lysine residues, or the therapeutic molecule can be conjugated to the ligand by means of hetero- or homo-bifunctional cross-linkers. Linker groups can be small organic compounds or peptides substituted with chemical linkers for conjugation. Examples of cleavable linkers include acid labile linkers, such as N-succinimidyl-3-(2-pyridyldithio)prioprionate (SPDP), cis-aconitic acid, cis-carboxylic alkadienes, cis-carboxylic alkatrienes, and poly-maleic anhydrides. Other cleavable linkers are linkers capable of attaching to primary alcohol groups.

In one embodiment, a linker comprising a proteolytic cleavage recognition sequence for a protease can be used to couple the therapeutic molecule to the transcytotic receptor ligand. Such proteolytic cleavage recognition sequences can be used to restrict release of the therapeutic molecule to sites of active infection characterized by high levels of protease activity. Examples include matrix metalloproteinase (MMP)-activated, epidermal growth factor-targeted retrovirus vectors (79), prostate-specific antigen protease-mediated activation of a doxorubicin-peptide prodrug (80), and human neutrophil elastase (HNE)-mediated activation of fusogenic peptide-liposome conjugates (81). Elastase and cathepsin G are proteases which are contained in the primary granules of neutrophils and are found at high levels at sites of infection. While the majority of proteases exist as zymogens whose activation results from proteolytic cleavage, elastase and cathepsin G represent two exceptions that are found to be fully active in the storage granules of neutrophils. A toxic antibiotic effective against the infection can therefore be coupled to a transcytotic receptor ligand using a peptide linkage comprising a specific protease recognition site.

Elastase and cathepsin G share similar substrate specificities, although elastase is 70-fold more reactive toward its best substrate than cathepsin G is toward its best substrate (83). Elastase recognition sites which can be used include N-Ac-Ala-Ala-DOPE, Ala-Ala-Pro-Val, and MeO-Suc-Ala-Ala-Pro-Val-pNA (82, 83). The latter recognition site is an exact analog of the most effective chloromethyl ketone elastase inhibitor, MeO-Suc-Ala-Ala-Pro-Val-$CH_2Cl$ (84). This elastase synthetic peptide substrate has a p-nitroanilide (pNA)-containing amide bond immediately following the site of cleavage, to better resemble a natural polypeptide substrate, and the N-terminal MeO-Suc linkage increases the solubility of the peptide in water. Cathepsin G recognition sites include MeO-Suc-Ala-Ala-Pro-Met-pNA (82), Suc-Ala-Ala-Pro-Phe-pNA, and Suc-Ala-Ala-Pro-Lys-pNA (85). Thus, a recognition site and protease can be selected depending on the speed and concentration at which release of a particular therapeutic molecule is desired.

Diseases of the respiratory system which can be treated using bifunctional molecules of the invention include, but are not limited to, cystic fibrosis, asthma, and emphysema. Idiopathic inflammatory bowel diseases, such as Crohn's disease and ulcerative colitis, as well as inflammatory bowel diseases of established origin, such as viral, bacterial, and parasitic infections, can also be treated using the bifunctional molecules disclosed herein. Therapeutic molecules useful in treating these diseases can be targeted to the appropriate sites by coupling the therapeutic molecule to a transcytotic receptor ligand. For example, antibiotics, corticosteroids, or other effective therapeutic molecules, such as IL-10, can be targeted to the respiratory epithelium in patients with emphysema or asthma. Similarly, corticosteroids, antibiotics, immunosuppressive drugs, or other effective therapeutic molecules, such as IL-10, can be targeted to the intestinal epithelium of patients with Crohn's disease or ulcerative colitis.

In one embodiment of the invention, an antibiotic is targeted to a cell comprising a transcytotic receptor, such as pIgR. Preferably, the cell is an epithelial cell, such as an airway or intestinal epithelial cell. Antibiotics which can be targeted include, but are not limited to, aminoglycosides, such as amikacin, gentamicin, kanamycin, neomycin, streptomycin, and tobramycin; cephalosporins, such as cefamandole nafate, cefazolin, cephalexin, cephaloglycin, cephaloridine, cephalothin, cephapirin and cephradine; penicillins, such as amoxocillin, ampicillin, carbenicillin, cloaxacillin, dicloxacillin, methicillin, nafcillin, oxacillin, penicillin G, penicillin V, and ticarcillin; sulfonamides; polypeptide antibiotics, such as bacitracin, colistimethate, colistin, and polymyxin B; fluoroquinolones, such as ciproflaxin; tetracyclines, such as chlortetracycline, demeclocycline, doxycycline, methacycline, minocycline, oxytetracycline, and tetracycline; and miscellaneous antibiotics, such as chloramphenicol, clindamycin, cycloserine, lincomycin, erythromycin, rifampin, spectinomycin, vancomycin, viomycin, fosfomycin, fusidate sodium, and novobiocin.

In another embodiment of the invention, the bifunctional molecule is a fusion protein, comprising a single-chain Fv molecule directed against a human transcytotic receptor covalently linked to a therapeutic protein. In this embodiment, the single chain Fv molecule is the transcytotic receptor ligand. Genetically engineered single chain Fv (Fv) peptides have been synthesized which attach the carboxyl terminus of one variable domain to the amino terminus of the other with a peptide linker (27–29). These Fv fragments have been shown to bind specific antigens, such as the transferrin receptor (30), and have been used to localize fusion proteins to targeted cells. Investigators have used such chimeras to deliver fusion proteins containing recombinant toxins (e.g., Pseudomonas exotoxin) and selectively kill cells in vitro and in vivo that express the appropriate receptor (30,31). There is considerable experience in the art expressing such fusions and retaining function of both components. Different Fv fragments can be employed to target different receptors, permitting the targeting of alternative cells. For example, cancer cells have receptors which can be used to target toxins to cancer cells. One example of such a receptor is EGFRvIII. U.S. Pat. No. 5,212,290 discloses antibodies to such a cancer cell-specific receptor and is incorporated herein by reference.

In particular, bifunctional molecules of the invention are particularly well-suited for treating cystic fibrosis. Epithelial defenses are breached early in the life of patients with cystic fibrosis (CF). Once live bacteria reach their surface, the epithelial cells direct the initial inflammatory response by releasing interleukin-8 (IL-8) and interleukin-6 (IL-6) as well as reducing expression of interleukin-10 (IL-10). The chemoattractants, combined with increased expression of adhesion molecules for neutrophils, enhance inflammatory cell migration into the airways. Once there, the neutrophils, in an attempt to clear the bacteria, release lytic enzymes in the process. If the neutrophils remain adherent to the epithelium, these enzymes are released right at the epithelial surface. Both mechanical disruption of cells and even low concentrations of neutrophil elastase (NE) result in the greater release of pro-inflammatory mediators from the respiratory epithelium. Thus, the inflammatory response is further enhanced.

Several strategies to interrupt this cycle have been proposed. Augmenting the antibacterial defenses of the airway at the epithelial surface may be useful. Prevention of the escalation of the inflammatory responses engendered by the neutrophils migrating into the airway could be accomplished by preventing the action of elastase at the airway cell surface. Both antibiotics and antiproteases are available for clinical use. Unfortunately, the results of clinical studies examining the use of the antiprotease in patients with CF have been disappointing. The systemic administration of alpha$_1$-antitrypsin (A$_1$AT) is inefficient, and the levels achieved by the intravenous administration of the antiprotease are insufficient to inhibit the overwhelming amount NE in the lung of patients with CF. Aerosolized A$_1$AT should permit the direct delivery to the airways, but the antiprotease delivered by nebulization has been uneven and deposits the drug atop the mucus blanket rather than the critical site at the surface of the cell. The present invention circumvents these difficulties.

Using the present invention, a variety of functional proteins can be preferentially delivered to the respiratory epithelial surface. These include, but are not limited to, protein antibiotics, antibodies, cytokines, and enzymes. A$_1$AT and SLP 1 can also be targeted using fusion proteins or bifunctional molecules of the invention. For example, if Pseudomonas aeruginosa interacts with respiratory epithelial cells to stimulate the production of IL-8 and other pro-inflammatory mediators, then it may be crucial that antibacterial protection occurs right at the epithelial surface. Recombinant defensins or protegrins, endogenous antibacterial peptides, could also be delivered to the pericilliary space using bifunctional molecules of the invention. Indeed, such antibacterial peptides have been identified in human airway epithelial cells (8, 9). The function of certain defensins against Pseudomonas aeruginosa may be hindered by the altered electrolyte composition of ELF in the CF lung (32). Thus, salt-insensitive forms of these antibacterial peptides may be used if the sodium chloride concentration of the ELF is abnormal. Another intriguing strategy is coupling Colistin, an agent already in use to treat pulmonary infections in patients with CF (33), to anti-human SC Fv. Killing Pseudomonas at the epithelial surface may be of value if it is the interaction of the bacteria and epithelial cell that incites the inflammatory process. Anti-inflammatory cytokines can also be transported to the epithelial surface (34), and pulmonary inflammation can be blocked by the specific delivery of interleukin-10 (IL-10), which can prevent the influx of neutrophils in the airway.

SLPI has potential advantages over A$_1$AT as the antiprotease component of the bifunctional molecule. SLPI is a potent antagonist of serine proteases that accounts for the majority of elastase inhibitory capacity of endobronchial secretions, and it also does not require glycosylation for its function or stability in serum (11, 12). For example, a fusion protein can be produced using a gene which encodes a bifunctional protein containing anti-human SC Fv linked to SLPI using the techniques described above. The entire SLPI cDNA from human respiratory epithelial cells can be amplified using primers for the antiprotease gene. Specific sites of recognition for restriction endonucleases, including a unique ClaI site, can be incorporated in human SLPI oligonucleotide primers to permit cloning into an expression vector. The gene encoding the SLPI can be inserted "in frame" into the cloning vector, the plasmid pRc/CMV, downstream to anti-human secretory component single chain Fv from monoclonal antibodies. The sequence of the chimeric gene can be readily confirmed. Other proteins which may be used as therapeutic components of a fusion protein include cytokines, interleukin-2, interleukin-10, and peptide antibiotics.

The fusion protein can comprise other polyamino acid sequences in addition to the single chain antibody and the therapeutic protein. Linker regions may be desirable to space the two portions of the protein from each other and to provide flexibility between them. Typically these will be less than 30 amino acid residues and will consist of predominantly neutral residues. Other moieties may also be included, as desired. These may include a binding region, such as avidin or an epitope, which may be useful for purification and processing of the fusion protein or modification of the fusion protein for chemical coupling of a small molecule. In addition, detectable markers may be attached to the fusion protein, so that the traffic of the fusion protein through a body or cell may be monitored conveniently. Such markers may include radionuclides, enzymes, fluors, etc.

The bifunctional molecules of the invention are particularly useful for administration to epithelial cells. Airway epithelial cells and intestinal lumen cells are particularly good targets for the molecules. While any mode of administration to these organs will work, such as targeted or localized administration modes, the bifunctional molecules of the present invention can be administered systemically, for example by intravenous, intramuscular, or subcutaneous injection, or by inhalation. The trancytotic receptor ligand portion of the molecule provides an excellent means of targeting, thus alleviating the need for targeted means of administration.

Suitable dosages for administration can be readily determined and will depend somewhat on the therapeutic molecule being delivered. However, typical dosage ranges will be between 0.05 mg and 5000 mg, preferably between 0.5 mg and 500 mg, and more preferably between 1 mg and 50 mg or between 5 and 50 mg. Due to the targeted nature of the molecule, lower dosages of the therapeutic molecule can be used than would be required when administering the therapeutic molecule alone. In the case of the delivery of antiproteases to the cystic fibrosis lung, for example, approximately 10–100 mg, preferably 70 mg, would need to be administered intravenously to achieve protection against neutrophil elastase.

The following examples provide specific modes of carrying out the invention. However, the invention is not limited or defined by the scope of these examples.

EXAMPLE 1
Targeting the Polymeric Immunoglobulin Receptor in vitro

We have shown that a complex consisting of the Fab portion of rabbit-derived, polyclonal antibody raised against human SC covalently linked to poly (L-lysine) will bind and condense plasmid DNA (38). The complexes effectively delivered foreign genes to human tracheal epithelial cells in culture which were induced to express pIgR (38). Human tracheal epithelial cells grown on plastic, a condition that down-regulates the expression of the receptor, fail to express the reporter gene, whereas cells from the same trachea maintained on collagen gels can be transfected. Therefore, delivery is specific for cells in culture that express the receptor.

Delivery of DNA is inhibited by excess human SC in the medium, which presumably occupies the recognition site on the Fab fragment, preventing its interaction with the receptor. However, competition for the pIgR with dIgA in a four-fold molar excess failed to block the delivery of the complex, perhaps indicating that the binding site(s) on the pIgR for dIgA and antibody do not overlap. Alternatively, the natural ligand may not compete effectively with the anti-human SC for the receptor, or the receptor may be present in excess. Uptake is not due to a non-specific increase in pinocytosis secondary to the presence of the Fab fragment in the culture medium, because the use of complexes with Fab fragments from irrelevant antibodies did not permit expression of reporter genes.

A variable percentage of human tracheal epithelial cells in primary culture were transfected through the pIgR. We have shown that differences in receptor expression in the cultured cells accounts for much of the observed variation. The proportion of human tracheal epithelial cells in culture which express pIgR which is detectable by immunofluorescence ranged from eight to thirty-five per cent, compared to five to sixty-six per cent of the cells which express the reporter gene delivered by the conjugate. The expression of the reporter gene co-localized to cells that expressed the receptor, as identified by immunohistochemical means. Thus, conjugates containing Fab fragments directed against human SC mediated the in vitro uptake of macromolecules into cells that expressed pIgR (38).

EXAMPLE 2
Targeting the Polymeric Immunoglobulin Receptor in vivo

We have examined the pattern of transport of the anti-rat SC Fab fragments in adult rats to determine if these antibodies have the same vascular distribution and clearance as dIgA. Fifty micrograms of the anti-rat SC antibodies were injected into the systemic circulation. Serial samples of bile and blood were collected every ten minutes and examined for the rabbit-derived antibody by enzyme-linked immunosorbent assay (ELISA). The anti-SC Fab was rapidly cleared from the blood, and the antibody appeared in the bile twenty minutes after infusion (FIG. 2). No uptake in the bile was noted after injection with pre-immune rabbit-derived Fab antibody (FIG. 2). The rat anti-SC Fab, however, was not detected in BAL fluid obtained two hours after injection, which may be related to the fifty-fold dilution of ELF. In addition, BAL preferentially samples the alveolar space, where the receptor is not expressed.

EXAMPLE 3
Gene Delivery Into Rats in vivo Using the pIgR

The pIgR was exploited for gene delivery into rats in vivo (39). Because the receptor is asymmetrically distributed, predominantly on the basolateral surface of epithelial cells, the complex should best be delivered by the systemic circulation. In our initial experiments, we tested the transfer of reporter genes into the lungs and livers of rats (39). Two tissues that do not express the pIgR, heart and spleen, were also tested as controls. Three hundred micrograms of the expression plasmid pGL2, consisting of the SV40 viral promoter and enhancer ligated to the *Photinus pyralis* luciferase gene inserted into the *Escherichia coli* pUC19 vector, complexed to the anti-SC Fab-polylysine conjugates were injected into the caudal vena cava of rats.

Luciferase expression was found in the homogenates from the liver and lungs, but not from the spleen or heart. No significant luciferase activity was detected in any tissue examined from animals treated with complexes containing either an irrelevant plasmid or the bona fide expression plasmid bound to a carrier based on an irrelevant Fab fragment. Thus, only tissues that contain cells bearing pIgR are transfected, and transduction cannot be attributed to nonspecific uptake.

Figure 14:
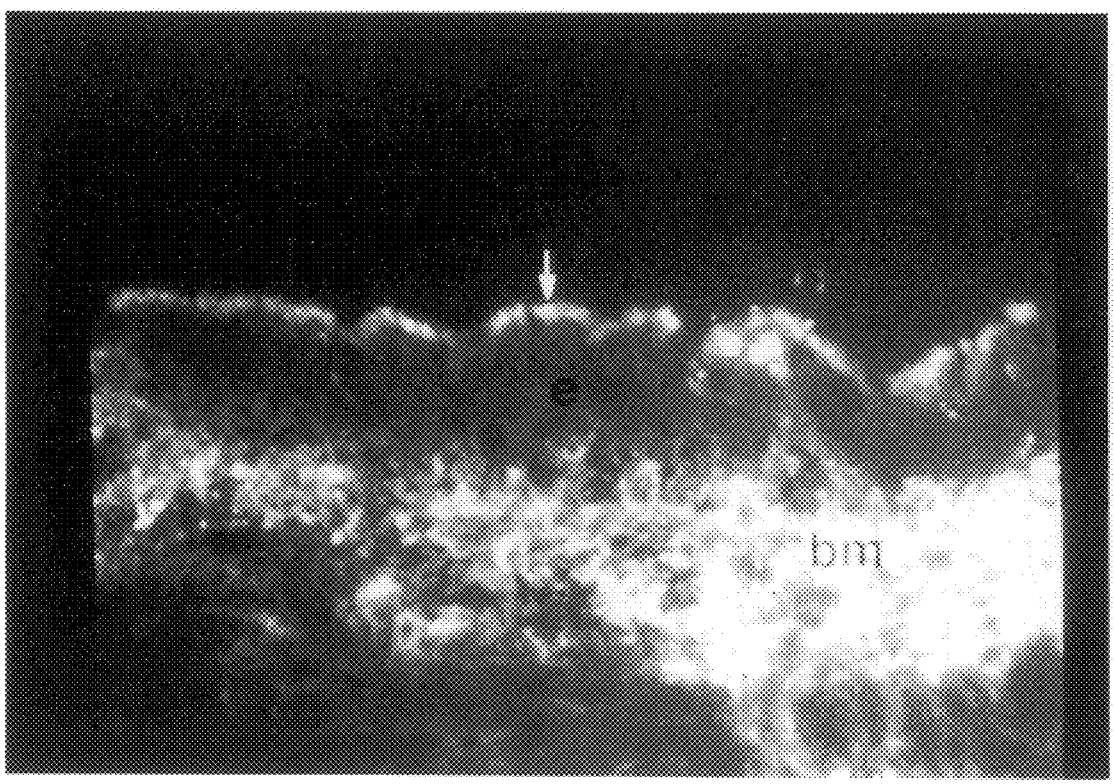
FIG. 14. IL-2 receptor gene transfer in vivo to rat tracheal epithelial cells by intravenous injection of pIgR-targeted PLASmin™ DNA. Arrow shows epithelial cells expressing human IL-2 receptor. Non-specific autofluorescencence was observed in the basement membrane layer (bm).

Specifically, transgene expression in the rats was greatest in the lung and less in liver, despite the recovery of the anti-rat SC Fab preferentially in bile. Thus, the airways are clearly accessed by the transfection complex in substantial amounts. When we examined cellular distribution of the transgene, seventeen per cent of the tracheal epithelial cells were positive for bacterial β-galactosidase. A more sensitive reporter (a human interleukin-2 receptor gene), however, showed that the majority of tracheal epithelial cells expressed the transgene (FIG. 14). These data demonstrate the ability of transfection complexes directed only by the anti-SC Fab to access airway epithelial cells after intravenous administration (39).

EXAMPLE 4

Modification of Molecular Conjugates to Reduce Their Immunogenicity

Figure 5:
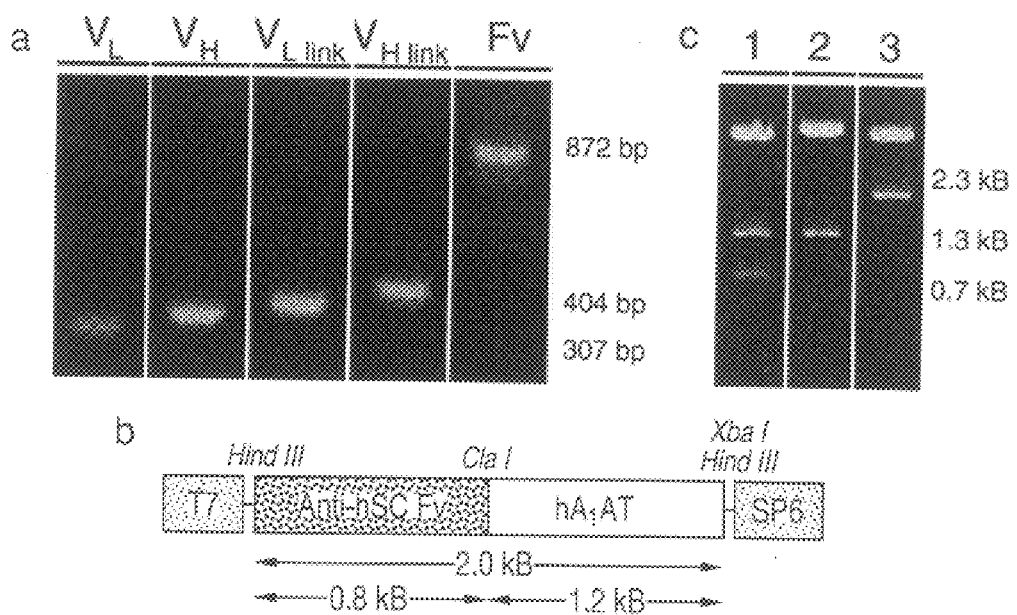
FIG. 5.

The molecular conjugates were subsequently modified to reduce their immunogenicity. Specifically, anti-SC Fv fragments were synthesized as ligands (FIG. 3). This approach requires the construction of monoclonal antibodies to replace the polyclonal antibodies used in the studies described above and preparation of a single chain Fv. This strategy removes the species-specific constant regions of the Fab, leaving only the framework regions in the variable domain that are still murine-specific.

EXAMPLE 5

Production of Monoclonal Antibodies Against the Human Polymeric Immunoglobulin Receptor Balb/c mice were hyperimmunized with purified human SC, which was isolated from human colostrum. The mice underwent intraperitoneal injections with human SC and subcutaneous injection with Freund's adjuvant and were bled weekly. An ELISA was used to detect the production of antibodies directed against human SC. Three of the five inoculated mice showed a substantial response in serum against the antigen two weeks after the second immunization. Spleens were harvested from two mice and used in fusion experiments with the SP2/0 mouse myeloma cell line using a standard approach for the generation of hybridomas (42).

The hybridoma cells were then placed in selective media containing hypoxanthine and thymidine, which eliminates myeloma cells that have not fused. The supernatants were analyzed for the production of anti-human SC antibodies. Positive hybridomas were cloned twice by limiting dilution. Several subclones continued to produce anti-human SC antibodies, as detected by ELISA. Monoclonal antibodies against human SC were generated, all of which cross-react with purified human SC (FIG. 4) and sIgA (FIG. 4). Therefore these antibodies most likely recognize epitopes other than the binding site of the natural ligand. Based on analysis using a fluorescence activated cell sorter (FACS), the monoclonal antibodies 4121 and 4214 were selected for the initial experiments, because they best recognized the receptor expressed on the surface of MDCK cells transduced with the cDNA encoding the human pIgR.

EXAMPLE 6

Expression Plasmids Encoding Fv Fragments of Anti-human Secretory Component

The $V_L$ and $V_H$ portions of the anti-human SC antibodies were cloned from the hybridoma cell lines. Total cellular RNA was extracted from the antibody-producing cells, and the mRNA transcripts were treated with Moloney Murine Leukemia Virus reverse transcriptase using random hexamers as primers. The resultant cDNA molecules were screened for the $V_L$ and $V_H$ domains using different oligonucleotide primers, as described by Nicholls and colleagues (43). These sequences were amplified by the polymerase chain reaction (PCR). The DNA sequences were spliced, separated by an interdomain linker that encodes fourteen or fifteen amino acids using a PCR technique called overlap extension (28, 43). Molecular modeling (44) and nuclear magnetic resonance analysis (45) have shown the optimal size of the linker in a single chain Fv to be greater than 12 amino acids. The use of glycine as the predominant amino acid in the linker permits the greatest molecular flexibility, thus allowing the two domains to fold properly and assume the proper orientation with each other. The cDNA encoding the $V_L$ and $V_H$ domains of the anti-human SC Fv were inserted into the expression vector downstream to the promoter for T3 RNA polymerase. The domains of the single chain Fv was assembled in the order $V_L$-linker-$V_H$, though either orientation can be used to produce functional Fv fragments. The anti-human SC Fv cDNA was sequenced by dideoxy chain termination.

EXAMPLE 7

Chimeric Genes Encoding Anti-secretory Component Fv and Human Alpha$_1$-antitrypsin The cDNA sequences encoding the anti-human SC Fv from monoclonal antibody 4121 and an irrelevant antibody directed against an anti-Pseudomonas polysaccharide (D8) were amplified through 30 cycles, using the following primers for the Fv: GG CCC AAG CTT GCC ACC ATG GAC ATT GTG CTG (SEQ ID NO:1), a primer to detect the 5' region, and CCT AGT CTA GAC TTA CAT CGA TGA GGA GAC TGT GAG AGT GGT GCC (SEQ ID NO:2), an antisense primer. The Kozak start sequence was placed immediately upstream of the Fv sequences to permit the optimal translation efficiency of the fusion protein in eukaryotes (46). Additional sequences encoding anti-human SC Fv isolated from other hybridoma clones can serve as alternative ligands.

The entire human $A_1AT$ cDNA was amplified, using the following primers for the human $A_1AT$ gene: GAG CCA TCG ATG CCG TCT TCT GTC TCG TGG (SEQ ID NO:3), a primer to the 5' end, and CCT AGT CTA GAT AAG CTT TTA TTT TTG GGT GGG ATT CAC (SEQ ID NO:4), an antisense primer which corresponds to the 3' end of the gene. Specific sites of recognition for the restriction endonucleases HindIII, ClaI, and XbaI in the Fv cDNA and the human $A_1AT$ primers were incorporated into both sets of primers to permit the excision of the intact chimeric gene and cloning into the expression vector "in-frame."

An *E. coli* cloning vector (pRc/CMV) was used to construct the anti-human SC Fv/human $A_1AT$ chimeric gene. The vector pRc/CMV is designed for high level, stable expression in eukaryotic cells and contains a multiple cloning site polylinker, cytomegalovirus promoter and enhancer, and bovine growth hormone polyadenylation signal. The vector also contains a neomycin resistance gene driven by the SV40 early promoter for the selection of stable transformants. This plasmid was digested with HindIII and XbaI, thus removing a segment of the multiple cloning site, and the amplified cDNA encoding the anti-human SC Fv was inserted. This construct was digested with ClaI and XbaI, and the amplified cDNA encoding human $A_1AT$ was ligated into this site in the same transcriptional orientation as the anti-SC Fv (FIG. 5). No episomal origin of replication is present in the plasmid. The nucleotide sequences of the 5' and 3' ends of the chimeric gene were examined by dideoxy chain termination, and no rearrangements were noted. The fidelity of the chimeric gene was verified by restriction site analysis (FIG. 5).

Once a chimeric gene is constructed, it can be shuttled into appropriate prokaryotic or eukaryotic expression vectors via HindIII sites on both termini. For expression in prokaryotes, the anti-human SC Fv/human $A_1AT$ chimeric gene was excised by digestion with HindIII, and ligated into the plasmid pQE-30 (Qiagen Inc., Chatsworth, Calif.). The gene is driven by the *E. coli* phage T5 and two lac operon sequences to eliminate expression prior to induction with isopropyl-β-D-thiogalactopyranoside (IPTG). This vector also contains a ribosome binding site and ampicillin resistance gene. A sequence encoding a polyhistidine (HHHHHH) label is located upstream in this vector, which permits the identification and purification of the translated recombinant protein on a nickel-NTA resin column (47). Both prokaryotic and eukaryotic expression plasmids containing the cDNA encoding the anti-human SC and human $A_1AT$ alone were constructed. A fusion protein containing an irrelevant anti-D8 Fv fragment ligated to the human $A_1AT$ was produced as control.

Figure 6:
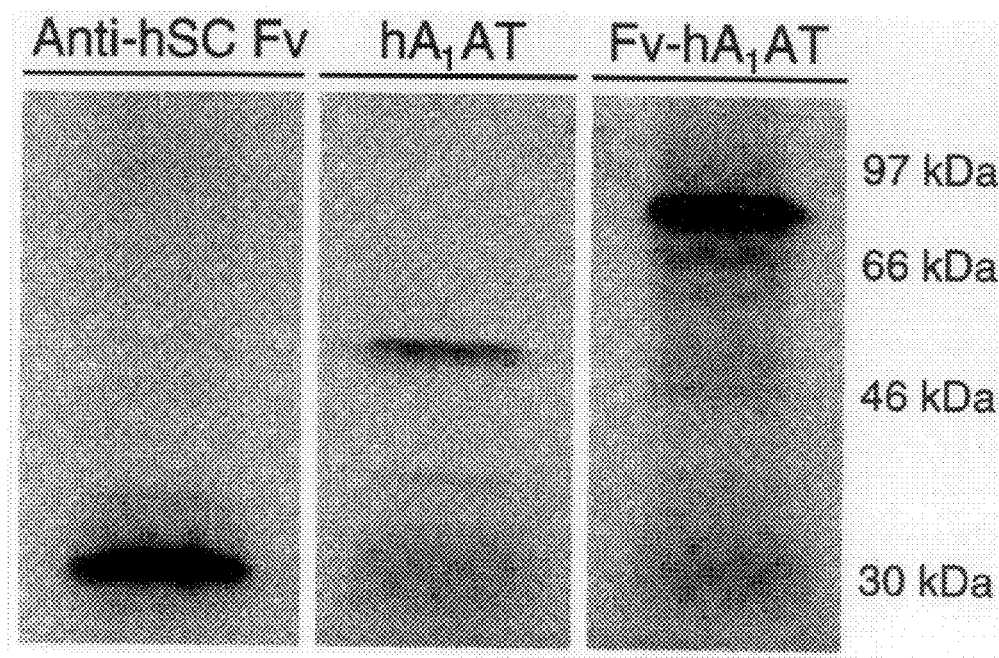
FIG. 6. In vitro transcription and translation of the anti-human SC Fv, human $A_1AT$, and anti-human SC Fv/human $A_1AT$ fusion proteins. Messenger RNA was translated using reticulate lysates, and [$^{35}$S]-labeled methionine was incorporated in the synthesized proteins. Analysis of the proteins by electrophoresis in SDS-polyacrylamide gels showed the presence of anti-human SC Fv, 26 kDa; human $A_1AT$, 52 kDa; and anti-human SC Fv/human $A_1AT$, 78 kDa.

In vitro transcription and translation of the chimeric gene was performed using a rabbit reticulocyte lysate system to determine if the chimeric gene encoding anti-human SC Fv/human $A_1AT$ could be expressed. Messenger RNA encoding the chimeric genes was generated by transcribing the expression plasmid with T7 RNA polymerase, which was then translated in reticulate lysates using a coupled TNT system (Promega, Madison, Wis.). The synthesized proteins were radiolabeled by adding [$^{35}$S] methionine to the translation reaction. Analysis of the lysates by electrophoresis in SDS-polyacrylamide gels demonstrated the presence of the appropriately sized proteins for the anti-human SC Fv, human $A_1AT$, and fusion protein (FIG. 6).

Figure 7:
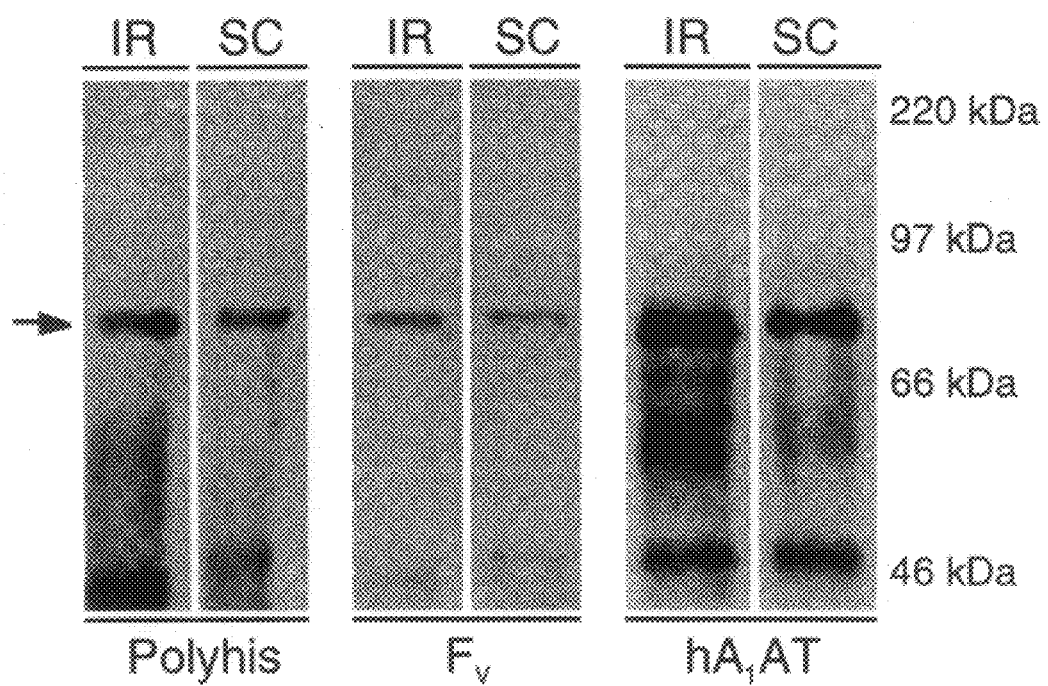
FIG. 7. Expression of anti-human SC Fv/human $A_1AT$ and anti-D8 Fv/human $A_1AT$ in prokaryotes. Protein extracts from bacterial clones obtained after transformation were purified by nickel-chelate affinity chromatography, subjected to electrophoresis in SDS-polyacrylamide gels, and transferred onto nitrocellulose membrane filters using established methods. The polyhistidine, single chain Fv, and human $A_1AT$ components were each identified by Western blot hybridization. The following samples were examined: anti-D8 Fv/human $A_1AT$ (IR), and anti-human SC Fv/human $A_1AT$ (SC). Arrow shows the expected molecular weight of the fusion. A lower molecular weight band was also present, most likely representing truncated fusion protein.

EXAMPLE 8
Production of Anti-human Secretory Component Fv/human Alpha$_1$-antitrypsin Fusion Protein in Prokaryotes Most single chain Fv constructs have been produced in bacteria, because prokaryotes can produce large quantities of fusion proteins. *E. coli* strain M15[pREP4] was transduced with a plasmid containing the anti-human SC Fv/human $A_1AT$ chimeric gene driven by the *E. coli* phage T5. Ampicillin resistant clones were selected in LB media containing 100 mg/ml ampicillin. Protein extracted from isolated inclusion bodies of transformed bacterial clones was purified by nickel-chelate affinity chromatography, which exploits the polyhistidine tag, subjected to electrophoresis in SDS-polyacrylamide gels, and transferred onto nitrocellulose membrane filters using established methods. The protein products were identified by Western blot analysis using antibodies directed against the individual components, i.e., polyhistidine tag, single chain Fv fragments, and human $A_1AT$, which demonstrated the same intact, non-glycosylated fusion protein (FIG. 7). Proteins from cytoplasmic inclusion bodies are inactive, so in order to recover function the Fv-based fusion proteins were solubilized and renatured by diluting resultant fusion proteins (48). We tried several refolding techniques, and dilution appears to be the most effective approach of renaturing the fusion protein produced in prokaryotes, although the efficiency of the process is uncertain.

Human $A_1AT$ is successfully made by *E. coli* and retains protease inhibition (49), but non-glycosylated forms of the antiprotease have extremely short half-lives in the circulation, decreasing the antiprotease half-life to hours (50). The shortened lifespan of the recombinant human $A_1AT$ may not be critical for our fusion proteins, however, because seventy-five percent of the anti-SC antibody is cleared from the circulation in one hour.

EXAMPLE 9
Recognition of the Human Secretory Component by Anti-human Secretory Component Fv ELISA was used to demonstrate that the single chain Fv portion of the fusion protein recognizes human SC. Human SC was incubated in each well of a 96 well microtiter plate, washed, and blocked. The fusion proteins synthesized by bacteria were isolated and refolded using standard techniques, then added to the wells. After washes, a rabbit-derived, polyclonal anti-human $A_1AT$ and a goat-derived, anti-rabbit (Fab')$_2$ conjugated with horseradish peroxidase were applied sequentially and used to detect the antiprotease portion of the protein.

Figure 8:
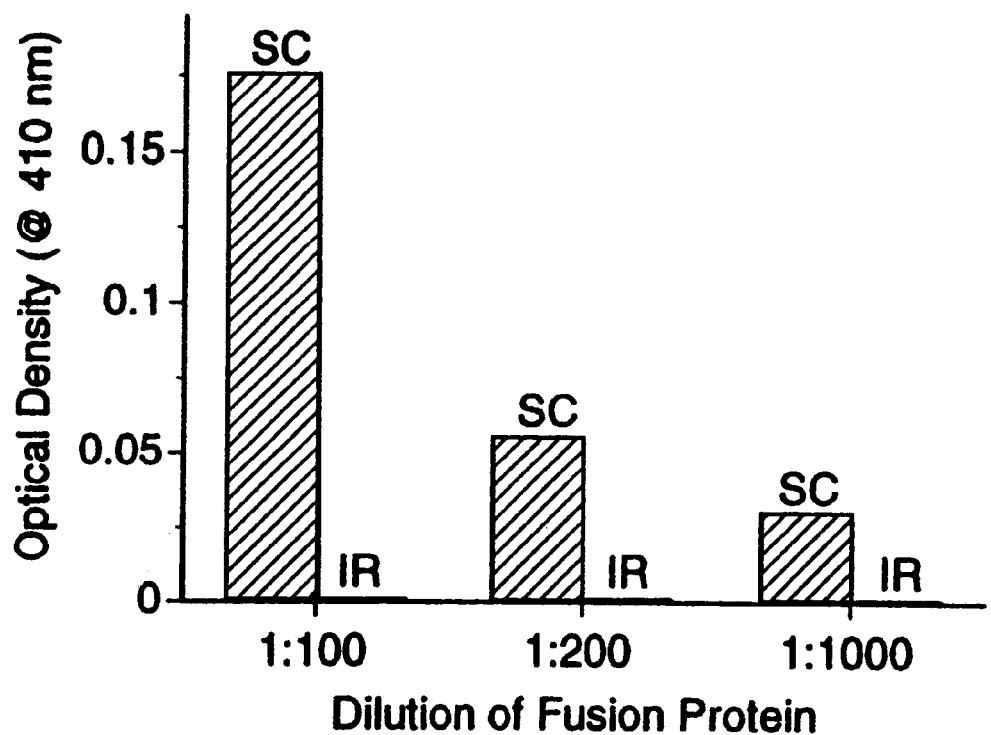
FIG. 8. Recognition of human SC by the anti-human SC Fv/human $A_1AT$, as measured by ELISA. The anti-human SC Fv-based fusion proteins (SC) bound to SC from human milk, indicating that the Fv portion is functional. Fusion proteins containing the irrelevant, anti-D8 Fv (IR) did not bind to human SC.

The fusion proteins containing the anti-human SC Fv effectively bound to the human secretory component, whereas fusions containing an irrelevant (anti-D8) Fv did not (FIG. 8). Because the Fv portion of the molecule recognizes human SC, the fusion protein used in later experiments could be purified by affinity column chromatography.

Thus, transformed bacteria can yield fusion proteins that recognize human SC, indicating that the single chain Fv component is functional. All three immunologically recognizable components of the fusion are present. The fusion protein is recognized by antibodies directed against both parts of the bifunctional protein, both by a commercially-available anti-human $A_1AT$ antibody and by an antibody we prepared against the framework regions covered by the oligonucleotide primers and used to generate the single chain Fv fragments. The polyhistidine tag from the expression vector was also recognized by the appropriate antibody.

EXAMPLE 10
Production of Anti-human Secretory Component Fv/human Alpha$_1$-antitrypsin Fusion Protein in Eukaryotic Cells Because they fail to process and glycosylate mammalian proteins appropriately, prokaryotes may not be the best system for expressing fusion proteins of the invention. Glycosylation stabilizes $A_1AT$ in the blood, although its antiprotease activity is unaffected. It is likely that stabilization will be more important for the native $A_1AT$ than for fusion proteins, which our data suggest will be rapidly directed to the site of action by the single chain Fv. Nevertheless, glycosylation of fusion proteins could be important and may represent an antigenic difference that is not desirable. Thus, it would be preferable to replicate the native $A_1AT$; the antiprotease component of the fusions may need to undergo post-translational processing by eukaryotic cells for this strategy to be successful.

Eukaryotic cells can effectively secrete single chain Fv proteins, which may be necessary for the large-scale production and purification of the fusion protein. The chimeric gene was altered to introduce an immunoglobulin light chain leader sequence to the 5' terminus of the Fv which will permit the secretion of the fusion protein by eukaryotic cells (51). The cDNA encoding the anti-human SC Fv from monoclonal antibody 4121 was amplified through 30 cycles, using the following primers for the immunoglobulin light chain leader sequence and Fv: GCG CCC AAG CTT GCC ACC ATG AGG ACC CCT GCT CAG TTT CTT GGA ATC TTG TTG CTC TGG TTT CCA GGT ATC AAA TGT GAC ATT GTG CTG ACC CAG TCT CC (SEQ ID NO:5), a primer to detect the leader sequence and 5' region of the single chain Fv and CCT AGT CTA GAC TTA CAT CGA TGA GGA GAC TGT GAG AGT GGT GCC (SEQ ID NO:2), an antisense primer. The Kozak start sequence was again inserted upstream to the leader sequence. Specific recognition sites for the restriction endonucleases HindIII, XbaI, and ClaI were included in the primers to permit ligation into a cloning vector. The vector pRc/CMV was used to assemble the chimeric gene encoding anti-human SC Fv/human $A_1AT$. This plasmid was digested with HindIII and XbaI, and the amplified cDNA encoding the anti-human SC Fv was inserted; this intermediate was digested with ClaI and XbaI, and cDNA encoding human $A_1AT$ ligated into the site in the same transcriptional orientation.

Insect cells have received considerable attention as prolific factories for proteins. We have also examined the synthesis of fusion proteins by transfected *Drosophila melanogaster* (S2) cells. The chimeric gene encoding anti-human SC Fv/human $A_1AT$ was ligated into the multiple cloning site of the pUC-hygMT expression plasmid at BamHI and XhoI sites in the same transcriptional orientation as the mouse metallothionein 1 promoter regulatory region (52). This vector also contains hygromycin and ampicillin resistance genes to permit selection. Using Lipofectin, S2 cells were transduced in suspension with the plasmid, and two days after transfection, expression of the transgene was induced by treating the cells with 0.5 mM copper sulfate for 24 hours (52). Cell lysates were collected and the proteins were separated by 10% SDS-polyacrylamide gel electrophoresis. The full length fusion protein was detected by Western blot hybridization using an anti-human $A_1AT$ antibody in cell lysates at concentrations of approximately 100 ng/ml. In preliminary studies, transfected S2 cells after selection secreted 3 to 5 $\mu$g/ml of the fusion protein into the media, as measured by ELISA that recognizes human SC.

EXAMPLE 11
Transcytosis of the Anti-secretory Component Antibodies and Fv Fragments Human tracheal epithelial cells grown in primary culture on collagen gels maintain production of pIgR. However, expression of the receptor differs among preparations. Cells stained in situ for human SC indicated that the expression of the production of pIgR in primary tracheal epithelial cells is variable, ranging from eight to thirty-five per cent of cells in culture, with a mean of twenty-two per cent by fluorescent activated cell sorter analysis. Because of this variability, the tracheal epithelial cells are not a suitable model for our investigations.

Figure 9:
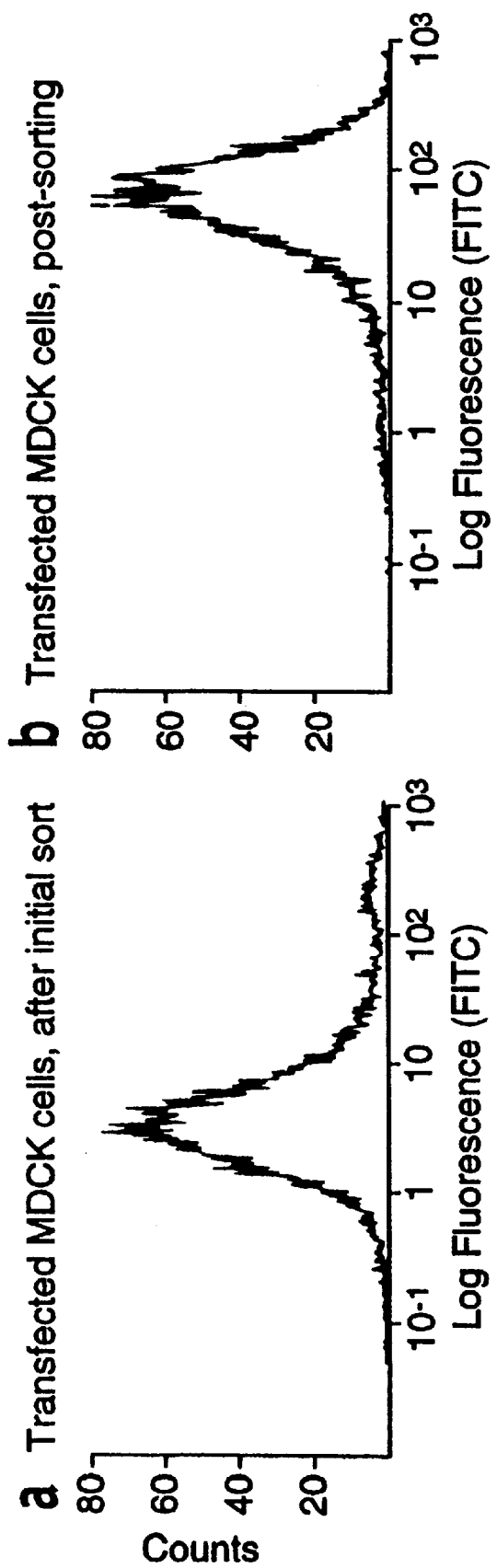
FIG. 9. Expression of the human pIgR in transfected MDCK cells from the initial sort after selection for neomycin resistance (FIG. 9A) and after serial sortings by fluorescent activated cell sorter analysis (FIG. 9B). Clones with the highest level of the pIgR expression were selected and used in subsequent experiments.

Madin-Darby canine kidney (MDCK) cells transfected with rabbit pIgR cDNA have been used extensively by several investigators as a method of examining the trafficking of the receptor (53, 54). We have developed a similar system for the transport of the human receptor in polarized cells. MDCK cells were transduced with the gene encoding the human pIgR. Stably transfected cells were selected for neomycin resistance, and positive cells were sorted repeatedly for the highest level of the human pIgR by a fluorescent activated cell sorter (FIG. 9). Individual, high expression cells were selected and expanded as clones. When grown on porous filters, the transduced MDCK cells appropriately traffic the human pIgR and the natural ligand dIgA from the basolateral to the apical membrane.

The transport of the anti-human SC monoclonal antibodies across the cells expressing the human pIgR was also examined. Fifty micrograms of the monoclonal antibodies 4121 and 4214 were applied to the basolateral surface of a monolayer of these cells. The anti-human SC monoclonal antibodies were transported to the apical surface, where they were released into the media (FIG. 10). Irrelevant monoclonal antibodies applied to the basolateral surface were not transported. None of the antibodies were trafficked across the cells in the opposite (i.e. apical-to-basolateral) direction. Thus, we have the ability to examine the transcytosis of proteins via the human pIgR, and we have used the cellular models to assess the efficiency of cellular transport of the bifunctional proteins.

Figure 11:
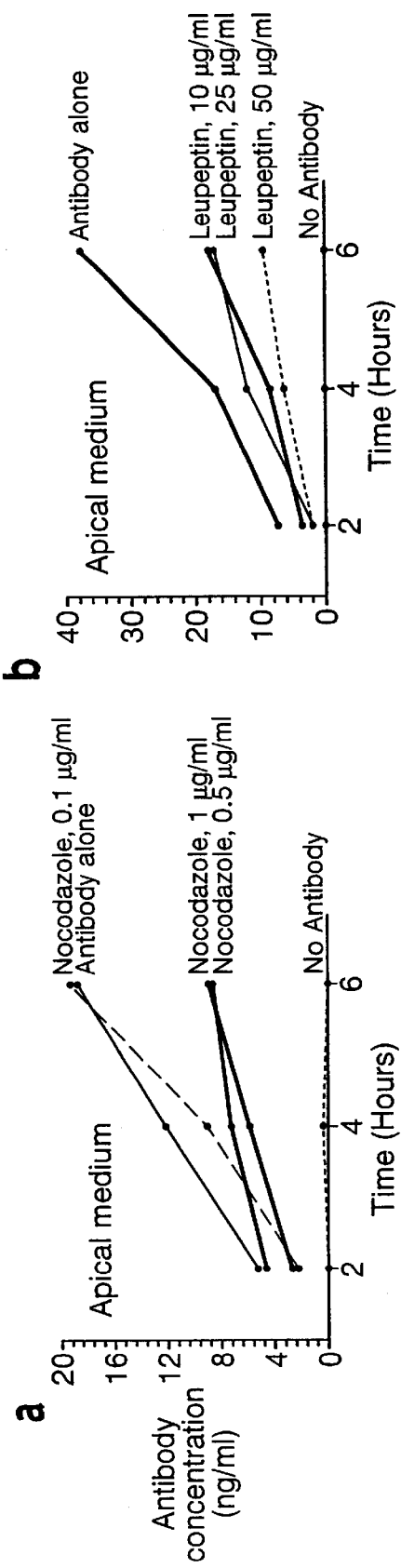
FIG. 11. Effect of nocodazole (FIG. 11A) and leupeptin (FIG. 11B) on transport of antibodies across transduced MDCK cells. Apical media was collected at different times after addition of the monoclonal antibody (4121) to the basolateral media, and the concentration (ng/ml) of the mouse-derived antibody was determined by ELISA. Both leupeptin and nocodazole reduced the amount of antibody detected in the apical medium in a dose-dependent fashion. Moreover, no transport of the antibody occurred in nontransfected MDCK cells or transduced cells in the apical-to-basolateral direction.

Epithelial cells have distinct apical and basolateral surfaces, and maintain their polarity with cytoskeletal elements. Microtubules are critical for fusion of endosomal vesicles, transcytosis of several proteins, and apical recycling. Colchicine and nocodazole (55, 56), agents that disrupt microtubule function, are reported to disrupt pIgR transcytosis while sparing endocytosis process. We examined the effects of nocodazole on the trafficking of monoclonal anti-human SC antibody across transduced MDCK cells that express the receptor. Fifteen micrograms of the intact monoclonal antibody was added to the basolateral media, and apical media was collected at different times. Nocodazole (concentration range, 0.1–1 $\mu$g/ml) markedly reduced the transcytosis of anti-human SC antibody (FIG. 11).

Once the pIgR and antibody reach the apical surface of the cell, the extracellular portion of the receptor is cleaved and the ligand, still bound to SC, is released at the apical surface. If cleavage does not occur, SC will not be released. We tested the ability of leupeptin, which inhibits the cleavage of pIgR, to block the release of the monoclonal antibody (57). Indeed, increasing concentrations of leupeptin (concentration range, 10–100 $\mu$g/ml) reduced the amount of antibody detected in the apical medium (FIG. 11).

Figure 12:
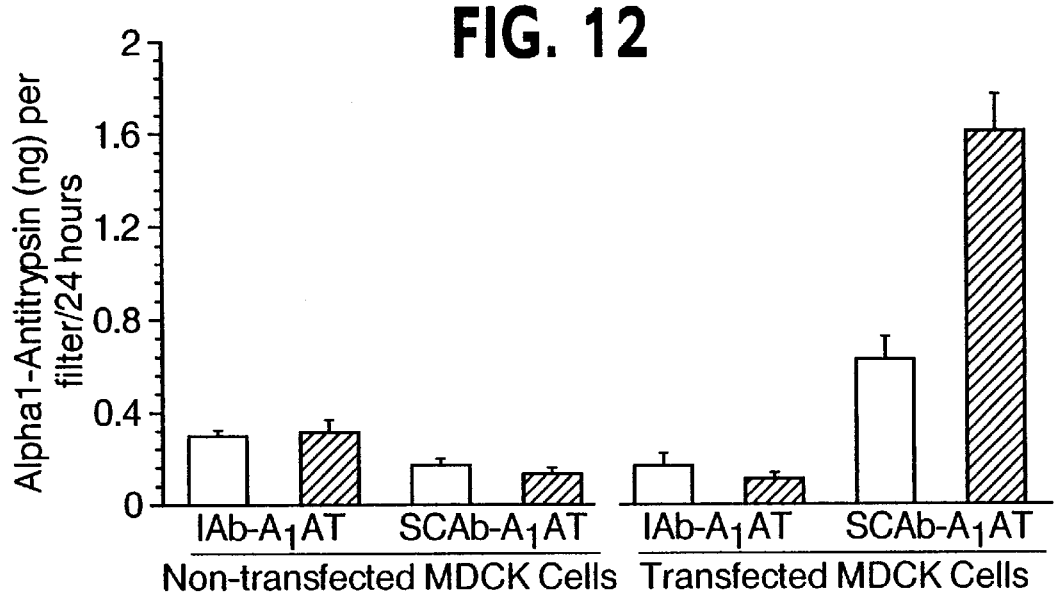
FIG. 12. Transport of anti-human SC-based protein conjugates across a cell monolayer. Twenty-four hours after addition of 1 μg of the conjugate to the basolateral or apical media, media was collected from the apical or basolateral compartments, respectively. The amount of immunoreactive $A_1AT$ (ng) transported was determined by ELISA. The anti-human SC/human $A_1AT$ conjugate was effectively transported in the basolateral-to-apical direction (solid columns) across the MDCK cells that express the pIgR. Virtually no transcytosis of the fusion proteins occurred in the opposite, apical-to-basolateral direction (open columns). Nontransfected MDCK cells did not transport either the bona fide or irrelevant fusion protein (in each group, n=5).

We also examined the transcytosis of the intact anti-human SC antibody (4121) chemically conjugated to human $A_1AT$ across a monolayer of transduced MDCK cells that appropriately traffic the human pIgR. When grown on a collagen support, these cells are polarized and transport the pIgR from the basolateral to the apical membrane, where SC is released. Anti-rat SC immunoglobulin G was bound to human $A_1AT$ by the heterobifunctional cross-linking reagent N-succinimidyl 3-(2-pyridyldithio) proprionate (SPDP) using established techniques (38, 39). The resultant conjugate (1 $\mu$g $A_1AT$ content) was added to the basolateral media of a monolayer of these cells, media from the apical surface was collected at different times and examined for the presence of the human $A_1AT$ by ELISA. Conjugates containing irrelevant monoclonal antibodies (anti-D8) were examined in parallel as a control. Consistently, anti-human SC/human $A_1AT$ conjugate was transported in the basolateral-to-apical direction across the MDCK cells that express human pIgR (FIG. 12). The conjugate containing an irrelevant Fv was not transported across the monolayer. Virtually no transport of the fusion proteins occurred in the opposite, apical-to-basolateral direction.

Figure 13:
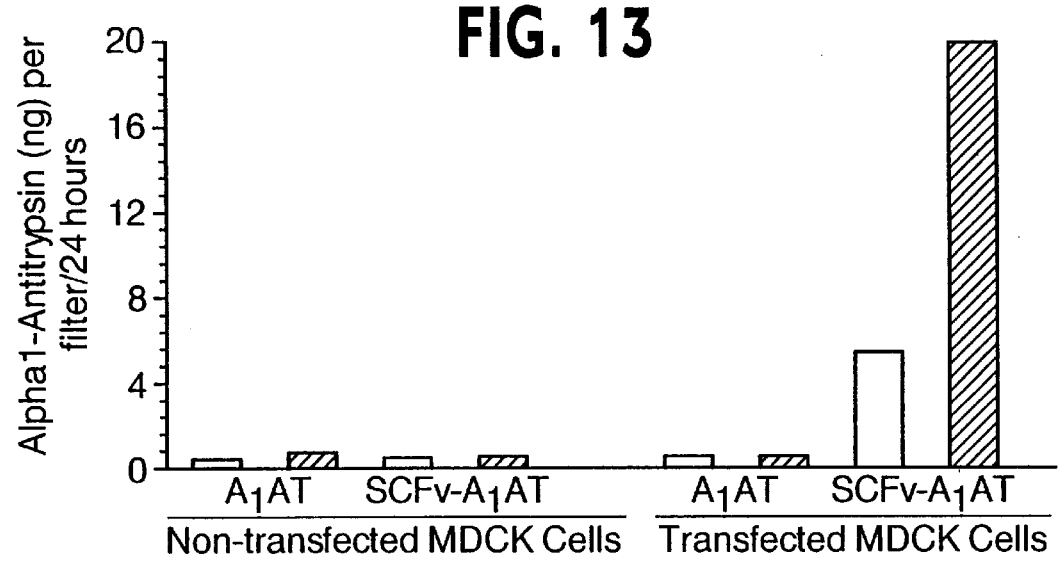
FIG. 13. Transport of fusion proteins across a cell monolayer. Twenty-four hours after addition of 2 μg of the fusions to the basolateral or apical media, media was collected from the apical or basolateral compartments, respectively, and the amount of immunoreactive $A_1AT$ (ng) transported was measured by ELISA. The anti-human SC Fv/human $A_1AT$ fusion was effectively transported in the basolateral-to-apical direction (solid columns) across the MDCK cells that express the pIgR. Considerably less of the fusion protein (approximately 25%) was transcytosed in the opposite, apical-to-basolateral direction (open columns). Purified human $A_1AT$ was not transported in either direction. Nontransfected MDCK cells did not transport either human $A_1AT$ or the fusion protein (in each group, n=5).

We also examined the transport of affinity purified fusion proteins containing the anti-human SC Fv (2 $\mu$g $A_1AT$ content) produced by stably transfected *D. melanogaster* S2 cells across cell monolayers. The fusions were effectively transported in the basolateral-to-apical direction across the receptor-expressing MDCK cells (FIG. 13). Substantially less fusion protein was transported across these cells in the opposite direction (FIG. 13). No purified human $A_1AT$ was transported across the monolayer in either direction. Neither the fusion protein or human $A_1AT$ was transported across a monolayer of non-transduced MDCK cells. In addition, fusion protein that was transported across the transduced MDCK cells to the apical compartment was bound to SC (refer to FIG. 1). The fusion proteins transported to the apical media were isolated by immunoprecipitation with a monoclonal antibody specific for human secretory component. The bound proteins were then subjected to electrophoresis in SDS-polyacrylamide gels and transferred onto a nitrocellulose membrane filter. The human $A_1AT$ component of the fusion was detected by Western blot hybridization. Neither the non-transported fusion nor the purified human $A_1AT$ was recognized by the anti-human SC antibody and precipitated. The uptake of the fusion, therefore, is mediated by the specific interaction of the anti-SC antibody with the human pIgR, and these constructs were transported to the apical surface of cells in vitro.

Figure 15:
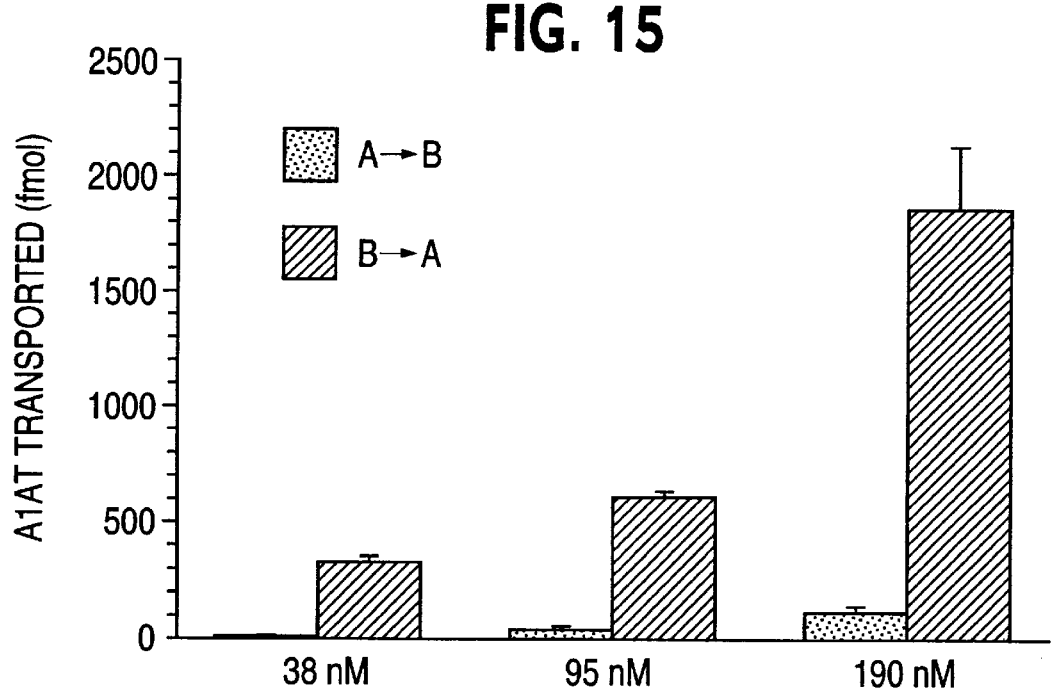
FIG. 15. Dose-response of transport of fusion proteins across a cell monolayer.

A dose-response experiment performed 24 hours after addition of increasing concentrations of the fusion protein to the basolateral or apical media (38, 95, and 190 nM) indicates that the basolateral-to-apical transportation of the fusion protein occurs in a dose-dependent manner (FIG. 15).

Figure 16:
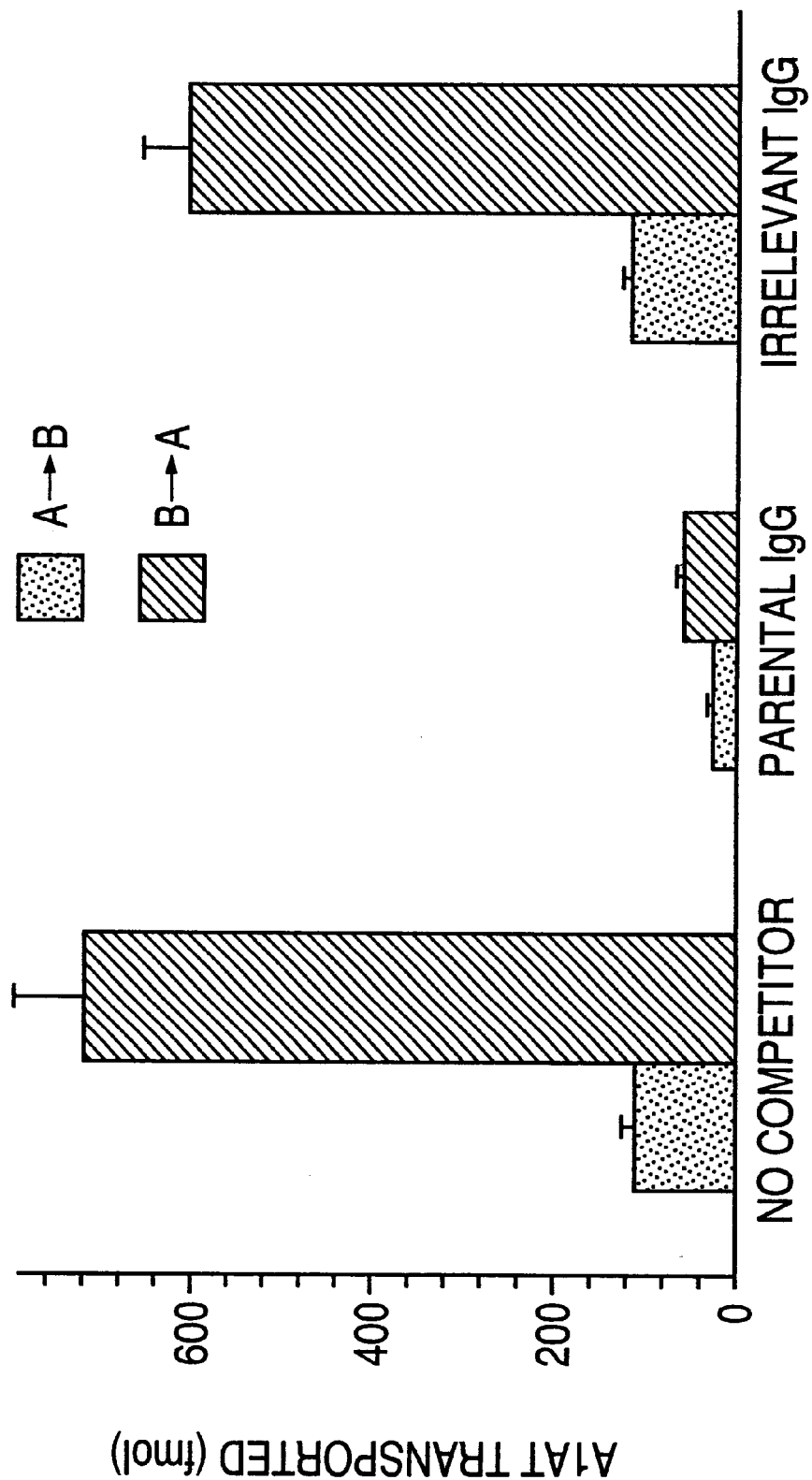
FIG. 16. Inhibition of fusion protein transport across receptor-bearing cells.

The fusion protein and a ten-fold molar excess of either the anti-secretory component monoclonal antibody or an irrelevant murine antibody were added to the basolateral or apical compartments, and the concentration (fmol) of the fusion protein in the opposite compartment was determined by ELISA. FIG. 16 shows that the parental antibody, but not the irrelevant antibody, reduced the amount of fusion protein detected in the apical media.

Figure 17:
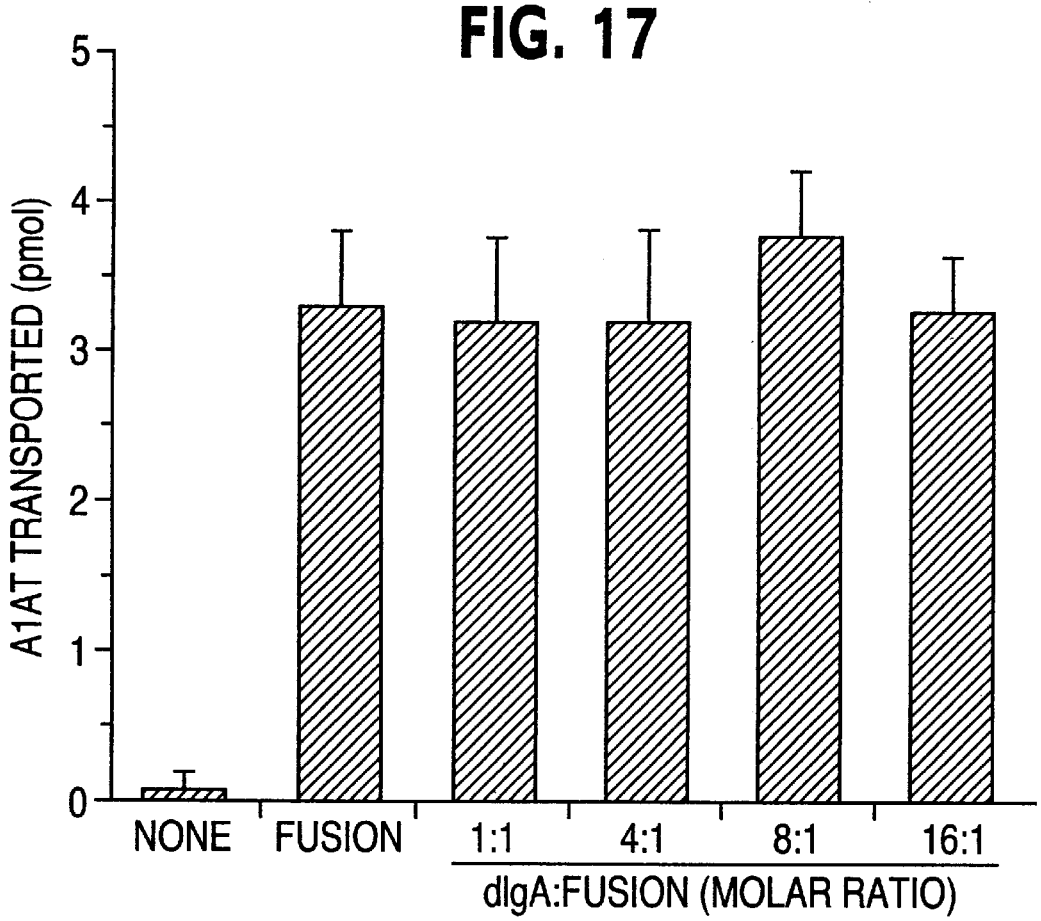
FIG. 17. Lack of inhibition of fusion protein transport by dimeric IgA.
Figure 18:
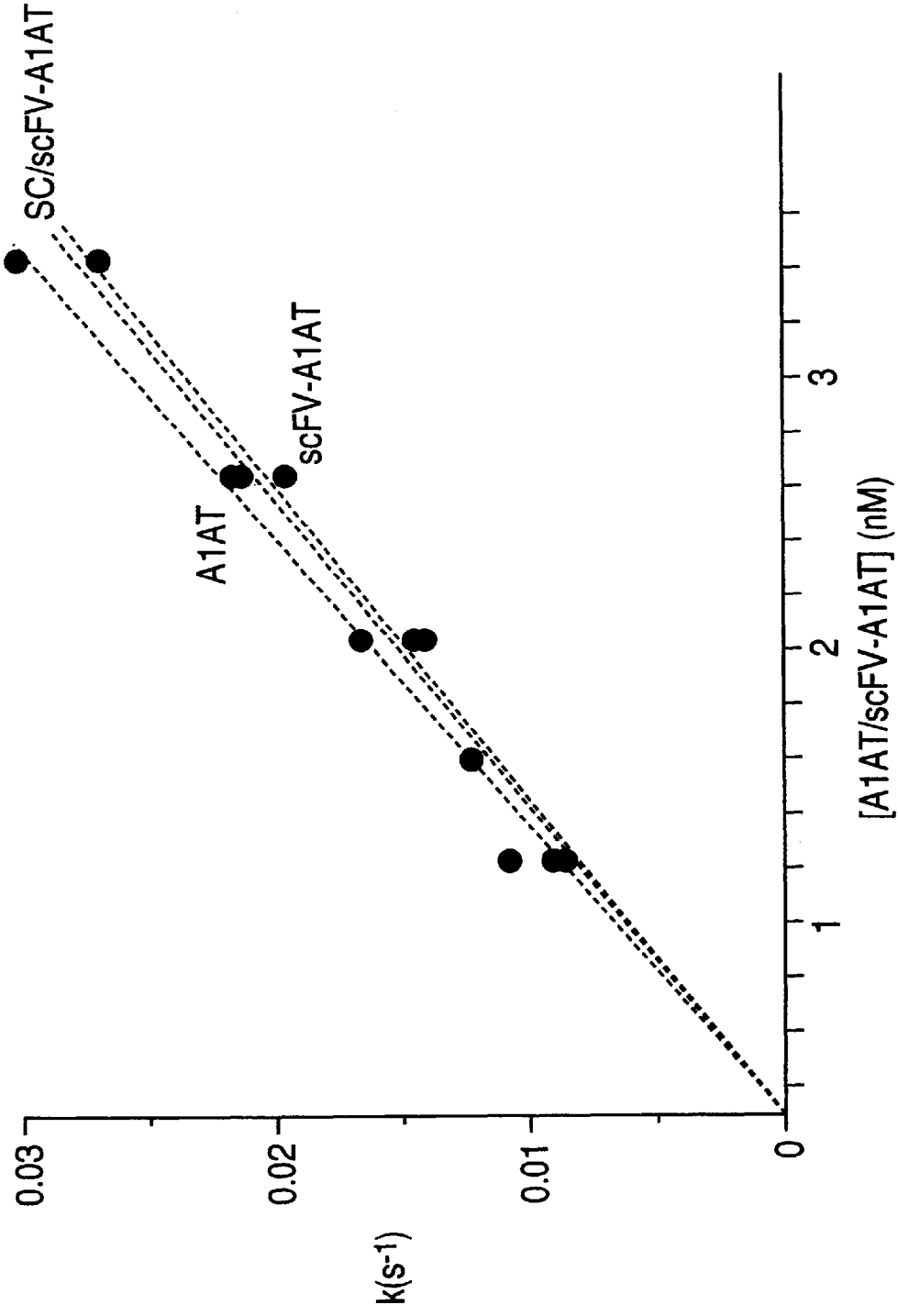
FIG. 18. Functional inhibition of neutrophil elastase by the fusion protein.

In addition, transcytosis of the fusion protein is not blocked by a up to a 16-fold molar excess of diameric IgA. (FIG. 17). This data suggests that intravenous infusion of the fusion protein in humans would not be inhibited by circulating IgA.

EXAMPLE 12
Antiprotease Activity of the Anti-human Secretory Component Fv/human Alpha$_1$-antitrypsin Fusion Protein The other component of the fusion protein, human $A_1AT$, was functional, based on the ability of the fusion to complex elastase. Inhibition of neutrophil elastase (NE) is the major physiological function of $A_1AT$, which neutralizes free elastase by permitting the enzyme to bind directly to a substrate-like region within the carboxy-terminus region of the antiprotease, resulting in a complex that contains one molecule of each of the reactants.

The fusion protein (100 ng $A_1AT$ content) was incubated with an equimolar amount of purified NE for 30 minutes at room temperature, and the resultant products were separated by SDS-polyacrylamide gel electrophoresis. Western blot hybridization of the products using a rabbit-derived, polyclonal anti-human $A_1AT$ showed a distinct size shift of the fusion protein. The human $A_1AT$ was partially degraded if excess antiprotease was added to the reaction. Moreover, human SC bound to the fusion did not appear to effect the binding of the antiprotease to elastase. Thus, both components of the anti-human SC Fv/human $A_1AT$ bifunctional protein are indeed functional.

EXAMPLE 13

Preparation of Fab-therapeutic Protein Conjugates

The Fab fragment of the anti-pIgR immunoglobulin G was covalently linked to a therapeutic protein using the heterobifunctional crosslinking reagent N-succinimidyl 3-(2-pyridyldithio) proprionate (SPDP). The Fab fragment was incubated with a seventy-five fold molar excess of SPDP in 0.1 M phosphate buffered saline (PBS), pH 7.5, at 22° C. for 60 minutes. After introduction of 2-pyridyl disulfide structures onto the Fab fragment, unreacted SPDP and low molecular weight reaction products were removed by dialysis. The disulfide bridges of the modified Fab fragment were cleaved with 2 mM dithiothreitol. Both the therapeutic protein and SPDP was added in fifteen fold molar excess to the modified Fab fragment, and the reaction was carried out at 22° C. for 24 hours. The conjugate was dialyzed to remove low molecular weight reaction products and analyzed by separating the resultant proteins on a 0.1% SDS-7.5% polyacrylamide gel electrophoresis.

EXAMPLE 14

Functional Inhibition of Neutrophil Elastase by an scFV-$A_1AT$ Fusion Protein

We measured the functional inhibition of neutrophil elastase by purified $A_1AT$, scFv-$A_1AT$ fusion protein, and fusion protein bound to human SC. Association reactions were initiated by adding $A_1AT$ (Calbiochem) or scFv$A_1AT$ to 0.6 nM purified human sputum elastase (Elastin Products Co., Owensville, Mo.) in 0.1 M Tris, 0.5 M NaCl, pH 7.5, at 23° C. To ensure that binding was measured under pseudo first-order conditions, the concentration of inhibitors was adjusted to 1.7–4.2 times the concentration of neutrophil elastase. The concentrations of the inhibitors were determined by titrations with standard neutrophil elastase.

The reactions were stopped at various times by adding substrate (N-methoxysuccinyl-ala-ala-pro-val p nitroanilide; Sigma) to a final concentration of 1.0 mM. A continuous assay trace was immediately recorded at 410 nm on a Cary 3A spectrophotometer (Varian). Background rates in the absence of neutrophil elastase were subtracted.

Assay rates, v, from association reactions were divided by control assay rates in the absence of these inhibitors to give a normalized value ($v_{(N)}$). These values were fitted by nonlinear regression analysis (FIG. P 6.0 for DOS, Biosoft, Ferguson, Mo.) to equation 1, where $V_{(N)initial}$ and $V_{(N)\ final}$ are the calculated values of $v_{(N)}$ at times zero and at equilibrium, respectively, and the observed pseudo first-order rate constant k for the approach to equilibrium is given by equation 2 (93).

$$v_{(N)}=v_{(N)\ final}+(v_{(N)\ initial}-v_{(N)\ final})e^{-k} \quad \text{equation 1}$$

where $$k=k_{assoc}[\text{inhibitor}]+k_{dissoc} \quad \text{equation 2}$$

In equation 2, $k_{assoc}$ is the associate rate, while $k_{dissoc}$ is the dissociation rate of the inhibitor binding to neutrophil elastase. Because the binding of $A_1AT$ to neutrophil elastase has been considered irreversible or pseudo-irreversible (15), $k_{dissoc}$ can be fixed to zero for the calculations of associate rate constants.

The $A_1AT$ domain of the fusion protein inhibited neutrophil elastase with an association rate constant of 0.79+/−$0.13\times10^7\ M^{-1}s^{-1}$, similar to that of plasma $A_1AT$ (0.87+/−$0.05\times10^7\ M^{-1}s^{-1}$). A similar association rate constant was observed for the transcytosed fusion protein.

EXAMPLE 15

Transport of Ligands Across Primary Airway Epithelial Cells in vitro and in vivo To demonstrate in vitro transport in primary human cells, anti-SC IgG (26 pmol/well) or dIgA (21 pmol/well) was added to the apical or basolateral surface of human bronchial epithelial cells in vitro. Twenty-four hours later, media and washings were collected from the apical and basolateral compartments. The amounts of human SC and ligands were measured by ELISA. FIG. 19 shows that ligands were transported from the basolateral to apical compartments in the human bronchial epithelial cells.

To demonstrate in vivo transport, anti-SC/scFV-$A_1AT$ fusion protein was injected intravenously into nude mice implanted with rat tracheal rings seeded with human bronchial epithelial cells. The explants were washed, and the amounts of human SC and ligands were measured by ELISA. Basolateral-to-apical transportation of the fusion protein also occurred in this in vivo model.

LITERATURE CITED

1. Konstan, M. W., Byard, P. J., Hoppel, C. L., and Davis, P. B. 1995. Effect of high dose ibuprofen in patients with cystic fibrosis. *N. Eng. J Med.* 332: 848–854.
2. Konstan, M. W., Hilliard, K. A., Norvell, T. M., and Berger, M. 1994. Bronchoalveolar lavage findings in cystic fibrosis patients with stable, clinically mild lung disease suggest ongoing infection and inflammation. *Am. J. Respir. Crit. Care Med.* 150: 448–454.
3. Richman-Eisenstat, J. B. Y., Jorens, P. G., Hebert, C. A., Ueki, I., and Nadel, J. A. 1993. Interleukin-8: an important chemoattractant in sputum of patients with chronic inflammatory airway disease. *Am. J. Physiol. Lung Cell Mol. Physiol.* 264: L413–418.
4. Lawrence, R. H. and Sorrelli, T. C. 1992. Decreased polymorphonuclear leucocyte chemotactic response to leukotriene $B_4$ in cystic fibrosis. *Clin. Exp. Immunol.* 89: 321–324.
5. Nakamura, H., Yoshimura, K., McElvaney, N. G., and Crystal, R. G. 1992. Neutrophil elastase in respiratory epithelial lining fluid of individuals with cystic fibrosis induces interleukin-8 gene expression in a human bronchial epithelial cell line. *J. Clin. Invest.* 89: 1478–1484.
6. Konstan, M. W. and Berger, M. 1993. Infection and inflammation of the lung in cystic fibrosis. In Davis, P. B. (ed.) Cystic Fibrosis. Marcel Decker, Inc. New York, N.Y. pp. 219–276.
7. Sommerhoff, C. P., Nadel, J. A., Basbaum, C. B., and Caughey, G. H. 1990. Neutrophil elastase and cathepsin G stimulate secretion from cultured bovine airway gland serous cells. *J. Clin. Invest.* 85: 682–689.
8. Goldman, M. J., Anderson, G. M., Stolzenberg, E. D., Kari, U. P., Zazloff, M., and Wilson, J. M. 1997. Human β-defensin-1 is a salt-sensitive antibiotic in lung that is inactivated in cystic fibrosis. *Cell.* 88: 553–560.
9. McCray, P. B., and Bentley, L. 1997. Human airway epithelia express a β-defensin. *Am. J. Resp. Cell. Mol. Biol.* 16: 343–349.
10. Rice, W. G. and Weiss, S. J. 1990. Regulation of proteolysis at the neutrophil-substrate interface by secretory leukoprotease inhibitor. *Science.* 249: 178–181.
11. Abe, T., Kobayashi, N., Yoshimura, K., Trapnell, B. C., Kim, H., Hubbard, R. C., Brewer, M. T., Thompson, R. C., and Crystal, R. G. 1991. Expression of the secretory leukoprotease inhibitor gene in epithelial cells. *J. Clin. Invest.* 87: 2207–2215.
12. Tegner, H. 1978. Quantitation of human granulocyte protease inhibition in non-purulent bronchoalveolar lavage fluid. *Acta Otolaryngol.* 85: 282–289.
13. Jin, F. Y., Nathan, C., Radzioch, D., and Ding, A. Secretory leukocyte protease inhibitor: a macrophage product induced by and antagonistic to bacterial lipopolysaccharide. *Cell.* 88: 417–426.
14. DiMango, E., Zar, H. J., Bryan, R., and Prince, A. 1995. Diverse *Pseudomonas aeruginosa* gene products stimulate respiratory epithelial cells to produce interleukin-8. *J. Clin. Invest.* 96: 2204–2210.
15. Morse J. O. 1978. Alpha$_1$-antitrypsin (two parts) *N Engl J Med.* 299: 1045–1048, 1099–1105.
16. Gadek, J. E., Fells, G. A., Zimmerman, R. L., Rennard, S. I., and Crystal, R. G. 1981. Antielastases of the human alveolar structures: implications for the protease-antiprotease theory of emphysema. *J. Clin. Invest.* 68: 889–898.
17. O'Connor, C. M., Gaffney, K., Keane, J., Southey, A., Byrne, N., O'Mahoney, S., and Fitzgerald, M. X. 1993. $\alpha_1$-Proteinase inhibitor, elastase activity, and lung disease severity in cystic fibrosis. *Am. Rev. Respir. Dis.* 148: 1665–1670.
18. Wewers M. D., Casolaro M. A., Sellers S. E., Swayse, S. C., McPhaul, K. M., Wittes, J. T., and Crystal, R. G. 1987. Replacement therapy for alpha$_1$-antitrypsin deficiency associated with emphysema. *N. Engl. J. Med.* 316: 1055–1062.
19. Hubbard R. C. and Crystal R. G. 1988. Alpha$_1$-antitrypsin augmentation therapy for alpha$_1$-antitrypsin deficiency. *Am. J Med.* 84 (suppl 6A): 52–62.
20. McElvaney, N. G., Hubbard, R. C., Birrer, P., Chernick, M. S., Caplan, D. B., Frank, M. M., and Crystal, R. G. 1991. Aerosol $\alpha_1$-antitrypsin treatment of cystic fibrosis. *Lancet.* 337: 392–394.
21. Brandzaeg, P. 1985. Role of J chain and secretory component in receptor-mediated glandular and hepatic transport of immunoglobulins in man. *Scand. J. Immunol.* 22: 111–146.
22. Breitfeld, P. P, Harris, J. M., and Mostov, K. E. 1989. Postendocytotic sorting of the ligand for the polymeric immunoglobulin receptor in Madin-Darby canine kidney cells. *J. Cell. Biol.* 109: 475–486.
23. Fiedler, M. A., Kaetzel, C. S., and Davis, P. B. 1991. Sustained production of secretory component by primary tracheal epithelial cells in primary culture. *Am. J. Physiol.* 261 (Lung Cell. Mol. Physiol.): L255–261.
24. Takamuri, T. and Eishi, Y. 1984. Distribution of SC and immunoglobulins in the developing lung. *Am. Rev. Respir. Dis.* 1318: 125–130.
25. Watts, C. L., Fanaroff, A. A., and Bruce, M. C. 1992. Fibronectin levels in lung secretions in respiratory distress syndrome. *J. Pediatr.* 20: 614–620.
26. Bird, R. E., Hardman, K. D., Jacobson, J. W., Johnson, S., Kaufman, B. M., Lee, S. M., Lee, T., Pope, S. H., Riordan, G. S., and Whitlow, M. 1988. Single-chain antigen-binding proteins. *Science.* 242: 423–426.
27. Huston, J. S., Levinson, D., Mudgett-Hunter, M., Tai, M. S., Novotny, J., Margolis, M. N., Ridge, R. J., Bruccoleri, R. B., Haber, E., Crea, R., Opperman, H. 1988. Protein engineering of antibody binding sites: recovery of specific activity in an anti-digoxin single chain Fv analogue produced in *Escherichia coli. Proc. Natl. Acad. Sci.* 85: 5879–5883.
28. Pantoliano, M. W., Bird, R. E., Johnson, S., Asel, E. D., Dodd, S. W., Wood, J. F., and Hardman, K. D. 1991. Conformational stability, folding, and ligand-binding affinity of single-chain Fv immunoglobulin fragments expressed in *Escherichia coli. Biochemistry.* 30: 10117–10125.
29. Colama, M. J., Hastings, A., Wims, L., and Morrison, S. 1992. Novel vectors for the expression of antibody molecules using variable regions generated by polymerase chain reactions. *J. Immunol. Meth.* 152: 89–104.
30. Batra, J. K., Fitzgerald, D. J., Chaudhary, V. K., and Pastan, I. 1991. Single-chain immunotoxins directed at the human transferrin receptor containing Pseudomonas exotoxin A or diphtheria toxin: anti-TFR(Fv)-PE40 and DT388-Anti-TFR(Fv). *Mol. Cell. Biol.* 11: 2200–2205.
31. Chaudhary, V. K., Queen, C., Junghans, R. P., Waldmann, T. A., FitzGerald, D. J., and Pastan, I. 1989. A recombinant immunotoxin consisting of two antibody variable domains fused to *Pseudomonas exotoxin. Nature.* 339: 394–397.

32 Smith, J. J., Travis, S. M., Greenberg, E. P., and Welsh, M. J. 1996. Cystic fibrosis airway epithelia fail to kill bacteria because of abnormal airway surface fluid. *Cell.* 85: 229–236.

33 Ramsey, B. W. 1996. Drug therapy: management of pulmonary disease in patients with cystic fibrosis. *N. Eng. J. Med.* 335: 179–188.

34 Bonfield, T. L., Konstan, M. W., Burfeind, P., Panuska, J. R., Hilliard, J. B., and Berger, M. 1995. Normal bronchial epithelial cells constitutively produce the antiinflammatory cytokine interleukin-10, which is down-regulated in cystic fibrosis. *Am.J.Respir.Cell Mol.Biol.* 13: 257–261.

35 Sullivan, D. A. and C. R. Wira. 1983. Variations in free secretory component levels in mucosal secretions of the rat. *J. Immunol.* 130: 1330–1335.

36 Huling, S., G. R. Fournier, A. Feren, A. Chuntharapai, and A. L. Jones. 1992. Ontogeny of the secretory immune system: Maturation of a functional polymeric immunoglobulin receptor regulated by gene expression. *Proc. Natl. Acad. Sci. USA.* 89: 4260–4264.

37 Chintalacharuvu, K. R., A. S. Tavill, L. N. Louis, J.-P. Vaerman, M. E. Lamm, and C. S. Kaetzel. 1994. Disulfide bond formation between dimeric immunoglobulin A and the polymeric immunoglobulin receptor during hepatic transcytosis. *Hepatology.* 19: 162–173.

38 Ferkol, T., Kaetzel, C. S., and Davis, P. B. 1993. Gene transfer into respiratory epithelial cells by targeting the polymeric immunoglobulin receptor. *J. Clin. Invest.* 93: 2394–2400.

39 Ferkol, T., Perales, J. C., Kaetzel, C. S., Eckman, E., Hanson, R. W., and Davis, P. B. 1995. Gene transfer into airways in animals by targeting the polymeric immunoglobulin receptor. *J. Clin. Invest.* 95: 493–502.

40 Ferkol, T., Pellicena-Palle, A., Eckman, E., Perales, J. C., Redman, R., Tosi, M., and Davis, P. B. 1996. Immunologic responses of gene transfer into mice via the polymeric immunoglobulin receptor. *Gene Ther.* 3: 669–678.

41 Eastman et al. Fasciculin 2 binds to the peripheral site on acetylcholinesterase and inhibits substrate hydrolysis by slowing a step involving proton transfer during enzyme acetylation. 1995. *J. Biol. Chem.* 270: 19694–701.

42 Oi, V. T. and Herzenberg, L. A. 1980. Immunoglobulin-producing hybrid cell lines. In Mishell, B. B. and Shiigi, S. M. (eds.). Selected Methods in Cellular Immunology. W. H. Freeman, pp. 351–372.

43 Nicholls, P. J., Johnson, V. G., Blanford, M. D., and Andrew, S. M. 1993. An improved method of generating single-chain antibodies from hybridomas. *J. Immunol. Methods.* 165: 81–91.

44 Johnson, S. and Bird, R. E. 1991. Construction of single-chain Fv derivatives of monoclonal antibodies and their production in *Escherichia coli*. *Methods Enzymol.* 203: 88–97.

45 Freund, C., Ross, A., Guth, B., Plückthun, A., and Holak, T. A. 1993. Characterization of the linker peptide of a single-chain Fv fragment of an antibody by NMR spectroscopy. *FEBS Letters.* 320: 97–100.

46 Kozak, M. 1994. Determinants of translational fidelity and efficiency in vertebrate mRNAs *Biochemie.* 76: 815–821.

47 Hochuli, E., Bannwarth, W., Dobeli, H., Gentz, R., and St über, D. 1988. Genetic approach to facilitate purification of recombinant proteins with a novel metal chelate absorbent. *BioTechnology.* 6: 1321–1325.

48 Huston, J. S., Mudgett-Hunter, M., Tai, M. S., McCartney, J., Warren, F., Haber, E., and Opperman, H. 1991. Protein engineering of single-chain Fv analogs and fusion proteins. *Methods Enzymol.* 203: 46–78.

49 Courtney, M., Buchwalder, A., Tessier, L. H., Jaye, M., Benavente, A., Balland, A., Kohli, V., Lathe, R., Tolstoshev, P., and Lecocq, J.-P. 1984. High-level production of biologically active human $\alpha_1$-antitrypsin in *Escherichia coli*. *Proc. Nat. Acad Sci., USA.* 81: 669–673.

50 Travis, J., Owen, M. C., George, P., Carrell, R. W., Rosenberg, S., Hallewell, R. A., and Barr, P. J. 1985. Isolation and properties of recombinant DNA produced variants of human alpha$_1$-proteinase inhibitor. *J. Biol. Chem.* 260: 4384–4393.

51 Jost, C. R., Kurucz, I., Jacobus, C. M., Titus, J. A., George, A. J. T., and Segal, D. M. 1994. Mammalian expression and secretion of functional single-chain Fv molecules. *J. Biol. Chem.* 269: 26267–26273.

52 Pavlakis, G. N. and Hamer, D. H. 1983. Regulation of a metallothinein-growth hormone hybrid gene in bovine papilloma virus. *Proc. Natl. Acad. Sci., USA.* 80: 397–401.

53 Mostov, K. E. and Dietcher, D. L. 1986. Polymeric immunoglobulin receptor expressed in MDCK cells transcytosis IgA. *Cell.* 46: 613–621.

54 Mostov, K. E. 1994. Transepithelial transport of immunoglobulins. *Annu. Rev. Immunol.* 12: 63–84.

55 Breitfield, P. P., McKinnon, W. C., and Mostov, K. E. 1990. Effect of nocodazole on vesicular traffic to the apical and basolateral surfaces of polarized MDCK cells. *J. Cell. Biol.* 111: 2365–2373.

56 Nagura, H., Nakane, P. K., and Brown, W. R. 1979. Translocation of dimeric IgA through neoplastic colon cells in vitro. *J. Immunol.* 123: 2359–2368.

57 Musil, L. S. and Baenziger, J. U. 1987. Cleavage of membrane secretory component to soluble secretory component occurs at the cell surface of rat hepatocyte monolayers. *J. Cell. Biol.* 104: 1725–1733.

58 Moritz, D. and Groner, B. 1995. A spacer region between the single chain antibody and the CD3$\epsilon$-chain domain of the chimeric T cell receptor components is required for efficient ligand binding and signaling activity. *Gene Ther.* 2: 539–546.

59 Konstan, M. W., Hilliard, K. A., Norvell, T. M., and Berger, M. 1994. Bronchoalveolar lavage findings in cystic fibrosis patients with stable, clinically mild lung disease suggest ongoing infection and inflammation. *Am. Rev. Respir. Crit. Care Med.* 150: 448–454.

60 Ferkol, T., Mularo, F., Hilliard, J., Lodish, L., Perales, J. C., Ziady, A. G., and Konstan, M. W. 1998. Transfer of the human alpha$_1$ antitrypsin gene into pulmonary macrophages in vivo. *Am. J. Respir. Cell. Mol. Biol.* 18: 591–601.

61 Travis, J. 1988. Structure, function, and control of neutrophil proteinase. *Am. J. Med.* 84: 37–42.

62 Stetler, G., Brewer, M. T., and Thompson, R. C. 1986. Isolation and sequence of a gene encoding a potent inhibitor of leukocyte proteases. *Nucleic Acids Res.* 14: 7883–7896.

63 Glockshuber, R., Malia, M., Pfitzinger, I., and Plückthun, A. 1990. A comparison of strategies to stabilize immunoglobulin Fv fragments. *Biochemistry.* 29: 1362–1367.

64 Prasher, D. C., Eckenrode, V. K., Ward, W. W., Prendergast, F. G., and Cormier, M. J. 1992. Primary structure of the *Aequorea victoria* green fluorescent protein. *Gene.* 111: 229–233.

65 Inouye, S. And Tsuji, F. I. 1994. Aequorea green fluorescent protein: expression of the gene and fluorescent characteristics of the recombinant protein. *FEBS Letters.* 341: 277–280.

66 Flach, J., Bossie, M., Vogel, J., Corbett, A., Jinks, T., Willins, D. A., and Silver, P. A. 1994. A yeast RNA-binding protein shuttles between the nucleus and cytoplasm. *Mol. Cell. Biol.* 14: 8399–8407.

67 Bian, J., Lin, X., and Tang, J. 1995. Nuclear localization of HIV-1 matrix protein P17: the use of *A. victoria* GFP in protei tagging and tracing. *FASEB J.* 9: A1279 (Abstract).

68 Wang, S. And Hazelrigg, T. 1994. Implications for bcd mRNA localization from spatial distribution of exu protein in Drosophila oogenesis. *Nature.* 369: 400–403.

69 Loman, S, Radl, J., Jansen, H. M., Out, T. A., and Lutter, R. 1997. Vectorial transcytosis of dimeric IgA by the Calu-3 human lung epithelial cell line: upregulation by IFN-γ. *Am. J. Physiol.* 272 (Lung Cell Mol. Physiol.): L951–L958.

70 Kvale, D., Lovhaug, D., Sollid, M., and Brandtzaeg, P. 1988. Tumor necrosis factor-α upregulates expression of secretory component, the epithelial receptor for polymeric Ig. *J. Immunol.* 140: 3086–3089.

71 Phillips, J. O., Everson, M. P., Moldoveanu, Z., Lue, C., and J. Mestecky. 1990. Synergistic effect of IL-4 and INF-γ on the expression of polymeric Ig receptor (secretory component) and IgA binding by human epithelial cells. *J. Immunol.* 145: 1740–1744.

72 Balough, K., McCubbin, M., Weinberger, M., Smits, W., Ahrens, R., and Fick, R. 1995. The relationship between infection and inflammation in the early stages of lung disease from cystic fibrosis. *Pediatr. Pulmonol.* 20: 63–70.

73 Pier, G. B., Small, G. J., and Warren, H. B. 1990. Protection against mucoid *Pseudomonas aeruginosa* in rodent models of endobronchial infections. *Science* 249: 537–540.

74 Konstan, M. W., Vargo, K. M., and Davis, P. B. 1990. Ibuprofen attenuates the inflammatory response to *Pseudomonas aeruginosa* in a rat model of chronic pulmonary infection: Implications for antiinflammatory therapy in cystic fibrosis. *Am.Rev.Respir.Dis.* 141: 186–192.

75 Cash, H. A., Woods, D. E., McCullough, B., Johanson, W. G., and Bass, J. A. 1979. A rat model of chronic pulmonary infection with *Pseudomonas aeruginosa. Am. Rev. Respir. Dis.* 119: 453–459.

76 Rennard, S. I., Basset, G., Lecossier, D., O'Donnell, K. M., Pinkston, P., Martin, P. G., and Crystal, R. G. 1986. Estimation of volume of epithelial lining fluid recovered by lavage using urea as a marker of dilution. *J. Appl. Physiol.* 60: 532–538.

77 Bolender, R. P., Hyde, D. M., and Dehoff, R. T. 1993. Lung morphometry: A new generation of tools and experiments for organ, tissue, cell, and molecular biology. *Am. J. Physiol.* 265 (*Lung Cell. Mol. Physiol.*): L5210–548.

78 van Heeckeren, A., Ferkol, T., Zakem-Cloud, H., Hamedani, A., Mularo, F., Konstan, M., and Tosi, M. 1998 *Pseudomonas aeruginosa* gene transfer to airway cells in mice. *Gene Ther.* 5: 345–51.

79 Peng, K.-W. et al. A gene delivery system activatable by disease-associated matrix metalloproteinases. 1997. *Human Gene Ther.* 8: 729–38.

80 Denmeade, S. R. et al. Enzymatic activation of a doxorubicin-peptide prodrug by prostate-specific antigen. 1998. *Cancer Res.* 58: 2537–40.

81 Pak, C. C. et al., Triggerable liposomal fusion by enzyme cleavage of a novel peptide-lipid conjugate. 1998. *Biochim. Biophys. Acta* 1372: 13–27.

82 Zimmerman, M., and B. M. Ashe. 1977. Substrate specificity of the elastase and the chymotrypsin-like enzyme of the human granulocyte. *Biochim. Biophys. Acta* 480: 241–45.

83 Nakajima, K. et al. Mapping the extended substrate binding site of cathepsin G and human leukocyte elastase. 1979. *J. Biol. Chem.* 254: 4027–33.

84 Powers, J. C. et al. 1977. Specificity of porcine pancreatic elastase, human leukocyte elastase and cathepsin G. *Biochim. Biophys. Acta* 485: 156–66.

85 Polanowska, J. et al. Specificity of human cathepsin G. 1998. *Biochim. Biolphys. Acta* 1386: 189–98.

86 Wagner et al. The diversity of antigen-specific monoclonal antibodies from transgenic mice bearing human immunoglobulin gene miniloci. 1994. *Eur. J. Immunol.* 24: 2672–81.

87 Lonberg et al. Antigen-specific human antibodies from mice comprising four distinct genetic modifications. 1994. *Nature* 368: 856–59.

88 Green et al. Antigen-specific human monoclonal antibodies from mice engineered with human Ig heavy and light chain YACs. 1994. *Nature Genet.* 7: 13–21.

89 Jakobovits. Production of fully human antibodies by transgenic mice. 1995. *Curr. Opin. Biotechnol.* 6: 561–66.

90 Jakobovits et al. Production of antigen-specific human antibodies from mice engineered with human heavy and light chain YACs. 1995. *Ann. N.Y. Acad. Sci.* 764: 525–35.

91 Bruggemann & Neuberger. Strategies for expressing human antibody repertoires in transgenic mice. 1996. *Immunol. Today* 17: 391–97.

92 Mendez et al. Functional transplant of megabase human immunoglobulin loci recapitulates human antibody response in mice. 1997. *Nature Genet.* 15: 146–56.

93 Caflisch, A. 1996. Computational combinatorial ligand design: Application to human α-thrombin. *J. Comput. Aided Mol. Des.* 10: 372–96.

94 Moon, J. B. and Howe, W. J. 1991. Computer design of bioactive molecules: A method for receptor-based de novo ligand design. *Proteins* 11:314–28.

What is claimed is:

1. A bifunctional molecule, comprising:
   a ligand which specifically binds to a transcytotic receptor; and
   a non-protein therapeutic molecule, wherein the non-protein therapeutic molecule is coupled to the ligand such that the ligand can bind to the transcytotic receptor.

2. The bifunctional molecule of claim 1 wherein the transcytotic receptor is human secretory component of polymeric immunoglobulin receptor.

3. The bifunctional molecule of claim 1 wherein the therapeutic molecule is an antibiotic.

4. The bifunctional molecule of claim 1 wherein the ligand is a single chain Fv.

5. The bifunctional molecule of claim 1 wherein the ligand is an antibody.

6. The bifunctional molecule of claim 1 wherein the ligand is a monoclonal antibody.

7. The bifunctional molecule of claim 1 wherein the ligand is a F(ab')$_2$, Fab or Fab' fragment.

8. The bifunctional molecule of claim 1 wherein the non-protein therapeutic molecule is coupled to the ligand by means of a linker comprising a proteolytic cleavage recognition sequence.

9. The bifunctional molecule of claim 8 wherein the proteolytic cleavage recognition sequence is specific for neutrophil elastase.

10. The bifunctional molecule of claim 8 wherein the proteolytic cleavage recognition sequence is specific for cathepsin G.

11. A method of delivering a therapeutic molecule to an epithelial cell comprising:
    administering to a patient a bifunctional molecule of claim 1, whereby the therapeutic molecule is delivered to an epithelial cell.

12. The method of claim 11 wherein the transcytotic receptor is human secretory component of polymeric immunoglobulin receptor.

13. The method of claim 11 wherein the epithelial cell is an airway epithelial cell.

14. The method of claim 11 wherein the epithelial cell is an intestinal lumen cell.

15. The method of claim 11 wherein the step of administering is performed by intravenous administration.

16. The method of claim 11 wherein the step of administering is performed by inhalation.

* * * * *

UNITED STATES PATENT AND TRADEMARK OFFICE
CERTIFICATE OF CORRECTION

PATENT NO. : 6,261,787 B1
DATED : July 17, 2001
INVENTOR(S) : Pamela B. Davis et al.

It is certified that error appears in the above-identified patent and that said Letters Patent is hereby corrected as shown below:

<u>Title page,</u>
Item [75], Inventors, "heights" has been replaced with -- Heights --
Item [56], References Cited, "a-thrombin" has been replaced with -- α-thrombin --
Item [56], References Cited, "Specifcity" has been replaced with -- Specificity --

Signed and Sealed this

Fourth Day of June, 2002

*Attest:*

JAMES E. ROGAN
*Attesting Officer*     *Director of the United States Patent and Trademark Office*

SEQUENCE LISTING

<160> NUMBER OF SEQ ID NOS: 5

<210> SEQ ID NO: 1
<211> LENGTH: 32
<212> TYPE: DNA
<213> ORGANISM: Homo sapiens

<400> SEQUENCE: 1

-continued

```
ggcccaagct tgccaccatg gacattgtgc tg                                    32

<210> SEQ ID NO: 2
<211> LENGTH: 45
<212> TYPE: DNA
<213> ORGANISM: Homo sapiens

<400> SEQUENCE: 2
cctagtctag acttacatcg atgaggagac tgtgagagtg gtgcc                      45

<210> SEQ ID NO: 3
<211> LENGTH: 30
<212> TYPE: DNA
<213> ORGANISM: Homo sapiens

<400> SEQUENCE: 3
gagccatcga tgccgtcttc tgtctcgtgg                                       30

<210> SEQ ID NO: 4
<211> LENGTH: 39
<212> TYPE: DNA
<213> ORGANISM: Homo sapiens

<400> SEQUENCE: 4
cctagtctag ataagctttt atttttgggt gggattcac                             39

<210> SEQ ID NO: 5
<211> LENGTH: 101
<212> TYPE: DNA
<213> ORGANISM: Homo sapiens

<400> SEQUENCE: 5
gcgcccaagc ttgccaccat gaggacccct gctcagtttc ttggaatctt gttgctctgg      60
tttccaggta tcaaatgtga cattgtgctg acccagtctc c                         101
```